(12) United States Patent
Ribble et al.

(10) Patent No.: US 11,367,535 B2
(45) Date of Patent: Jun. 21, 2022

(54) PATIENT CARE SYSTEM FOR A HOME ENVIRONMENT

(71) Applicant: Hill-Rom Services, Inc., Batesville, IN (US)

(72) Inventors: David L. Ribble, Batesville, IN (US); Craig M. Meyerson, Syracuse, NY (US); Lori Zapfe, Milroy, IN (US); John V. Harmeyer, Cleves, OH (US); Xuan Teng, Batesville, IN (US); Jotpreet Chahal, Fayetteville, NY (US); Thomas F. Heil, Batesville, IN (US); Kirsten M. Emmons, Batesville, IN (US); David L. Bedel, Oldenburg, IN (US); Kenneth L. Lilly, West Chester, OH (US); Nicholas Mann, Batesville, IN (US)

(73) Assignee: Hill-Rom Services, Inc., Batesville, IN (US)

( * ) Notice: Subject to any disclaimer, the term of this patent is extended or adjusted under 35 U.S.C. 154(b) by 135 days.

(21) Appl. No.: 16/583,348

(22) Filed: Sep. 26, 2019

(65) Prior Publication Data

US 2020/0105422 A1 Apr. 2, 2020

Related U.S. Application Data

(60) Provisional application No. 62/739,334, filed on Sep. 30, 2018.

(51) Int. Cl.
*G16H 80/00* (2018.01)
*G16H 50/30* (2018.01)
(Continued)

(52) U.S. Cl.
CPC .......... *G16H 80/00* (2018.01); *A61B 5/0022* (2013.01); *A61B 5/14542* (2013.01);
(Continued)

(58) Field of Classification Search
CPC .................................................. G16H 80/00
See application file for complete search history.

(56) References Cited

U.S. PATENT DOCUMENTS 948,644 A 2/1910 Bjornstad
1,610,898 A 12/1926 Steiner
(Continued)

FOREIGN PATENT DOCUMENTS

DE 1987293 A1 6/1968
JP S5438512 U 3/1979
(Continued)

OTHER PUBLICATIONS

Abo-Zahhad, M et al. "A wireless emergency telemedicine system for patients monitoring and diagnosis." International journal of telemedicine and applications vol. 2014 (2014): 380787. doi:10.1155/2014/380787 (Year: 2014).*
(Continued)

*Primary Examiner* — Sheetal R Paulson
(74) *Attorney, Agent, or Firm* — Barnes & Thornburg LLP

(57) ABSTRACT

An apparatus for remote at-home care of a patient is disclosed. The apparatus monitors a patient with a deployable sensor system and communicates the data sensed by the sensor system to a patient care hub located within a patient's home. A patient interface and a caregiver controller are in wireless communication with each other and the patient care hub. The patient care hub generates an alert(s) in view of the sensed data and wirelessly communicates the alert(s) to the patient interface and/or the caregiver controller.

22 Claims, 17 Drawing Sheets

(51) Int. Cl.
*A61B 5/00* (2006.01)
*A61B 5/145* (2006.01)
*A61G 7/10* (2006.01)

(52) U.S. Cl.
CPC ............ *A61B 5/742* (2013.01); *A61G 7/1021* (2013.01); *G16H 50/30* (2018.01); *A61G 2203/12* (2013.01)

(56) References Cited

U.S. PATENT DOCUMENTS

| | | |
|---|---|---|
| 2,612,645 A | 10/1952 | Gus |
| 2,887,692 A | 5/1959 | Clarence |
| 3,392,412 A | 7/1968 | Robert |
| 3,426,373 A | 2/1969 | Scott et al. |
| 3,606,623 A | 9/1971 | Robert et al. |
| 3,667,075 A | 6/1972 | Ballard |
| 3,781,928 A | 1/1974 | Swallert |
| 4,142,263 A | 3/1979 | Pierson |
| 4,150,284 A | 4/1979 | Trenkler et al. |
| 4,151,407 A | 4/1979 | Delagi et al. |
| 4,165,125 A | 8/1979 | Owen |
| 4,183,015 A | 1/1980 | Drew et al. |
| 4,216,462 A | 8/1980 | Digiacomo et al. |
| 4,225,953 A | 9/1980 | Simon et al. |
| 4,228,426 A | 10/1980 | Roberts |
| 4,237,344 A | 12/1980 | Moore |
| 4,298,863 A | 11/1981 | Natitus et al. |
| 4,309,783 A | 1/1982 | Cammack et al. |
| 4,331,953 A | 5/1982 | Blevins et al. |
| 4,527,298 A | 7/1985 | Moulton |
| 4,542,547 A | 9/1985 | Sato |
| 4,554,693 A | 11/1985 | Calloway |
| 4,577,185 A | 3/1986 | Andersen |
| 4,578,671 A | 3/1986 | Flowers |
| 4,593,273 A | 6/1986 | Narcisse |
| 4,598,275 A | 7/1986 | Ross et al. |
| 4,601,064 A | 7/1986 | Shipley |
| 4,649,385 A | 3/1987 | Aires et al. |
| 4,680,790 A | 7/1987 | Packard et al. |
| 4,814,751 A | 3/1989 | Hawkins et al. |
| 4,839,932 A | 6/1989 | Williamson |
| 4,850,040 A | 7/1989 | Teich et al. |
| 4,877,288 A | 10/1989 | Lee |
| 4,932,089 A | 6/1990 | Laviero |
| 4,955,000 A | 9/1990 | Nastrom |
| 4,967,195 A | 10/1990 | Shipley |
| 4,990,892 A | 2/1991 | Guest et al. |
| 4,998,095 A | 3/1991 | Shields |
| 4,998,939 A | 3/1991 | Potthast et al. |
| 5,012,539 A | 5/1991 | Grigg |
| 5,036,852 A | 8/1991 | Leishman |
| 5,060,174 A | 10/1991 | Gross |
| 5,062,151 A | 10/1991 | Shipley |
| 5,065,154 A | 11/1991 | Kaiser et al. |
| 5,086,290 A | 2/1992 | Murray et al. |
| 5,103,108 A | 4/1992 | Crimmins |
| 5,124,991 A | 6/1992 | Allen |
| 5,137,033 A | 8/1992 | Norton |
| 5,144,284 A | 9/1992 | Hammett |
| 5,153,584 A | 10/1992 | Engira |
| 5,170,522 A | 12/1992 | Walker |
| 5,184,112 A | 2/1993 | Gusakov |
| 5,195,198 A | 3/1993 | Travis |
| 5,253,656 A | 10/1993 | Rincoe et al. |
| 5,269,388 A | 12/1993 | Reichow et al. |
| 5,276,432 A | 1/1994 | Travis |
| 5,311,625 A | 5/1994 | Barker et al. |
| 5,345,630 A | 9/1994 | Healy |
| 5,353,012 A | 10/1994 | Barham et al. |
| 5,415,167 A | 5/1995 | Wilk |
| 5,432,967 A | 7/1995 | William |
| 5,490,295 A | 2/1996 | Boyd |
| 5,528,783 A | 6/1996 | Kunz et al. |
| 5,577,278 A | 11/1996 | Barker et al. |
| 5,621,931 A | 4/1997 | Hamilton |
| 5,715,548 A | 2/1998 | Weismiller et al. |
| 5,838,223 A | 11/1998 | Gallant et al. |
| 5,844,488 A | 12/1998 | Musick |
| 5,867,821 A | 2/1999 | Ballantyne et al. |
| 5,877,675 A | 3/1999 | Rebstock et al. |
| 5,933,488 A | 8/1999 | Marcus et al. |
| 5,936,539 A | 8/1999 | Fuchs |
| 5,942,986 A | 8/1999 | Shabot et al. |
| 5,944,659 A | 8/1999 | Flach et al. |
| 5,963,137 A | 10/1999 | Waters |
| 6,009,873 A | 1/2000 | Neviaser |
| 6,093,146 A | 7/2000 | Filangeri |
| 6,097,308 A | 8/2000 | Albert et al. |
| 6,111,509 A | 8/2000 | Holmes |
| 6,125,350 A | 9/2000 | Dirbas |
| 6,131,219 A | 10/2000 | Roberts |
| 6,133,837 A | 10/2000 | Riley |
| 6,142,592 A | 11/2000 | Grittke et al. |
| 6,183,417 B1 | 2/2001 | Geheb et al. |
| 6,208,250 B1 | 3/2001 | Dixon et al. |
| 6,397,416 B2 | 6/2002 | Brooke et al. |
| 6,684,425 B2 | 2/2004 | Davis |
| 7,154,397 B2 | 12/2006 | Zerhusen et al. |
| 7,568,246 B2 | 8/2009 | Weismiller et al. |
| 7,669,263 B2 | 3/2010 | Menkedick et al. |
| 7,690,059 B2 | 4/2010 | Lemire et al. |
| 7,852,208 B2 | 12/2010 | Collins, Jr. et al. |
| 8,536,990 B2 | 9/2013 | Collins, Jr. et al. |
| 8,656,541 B2 | 2/2014 | Muollo |
| 8,789,224 B2 | 7/2014 | Wyatt et al. |
| 9,805,163 B1 * | 10/2017 | Panch ................... G16H 40/67 |
| 2003/0041378 A1 | 3/2003 | Davis |
| 2003/0150058 A1 | 8/2003 | Davis |
| 2003/0196270 A1 | 10/2003 | Leventhal et al. |
| 2006/0117482 A1 | 6/2006 | Branson |
| 2006/0123550 A1 | 6/2006 | Davis |
| 2006/0230539 A1 | 10/2006 | Goodman |
| 2008/0147442 A1 | 6/2008 | Warner et al. |
| 2016/0235610 A1 * | 8/2016 | Drake ................... A61B 5/024 |
| 2016/0331616 A1 | 11/2016 | Fisk et al. |
| 2018/0103874 A1 * | 4/2018 | Lee ...................... A61B 5/6823 |
| 2018/0333082 A1 | 11/2018 | Hoffman et al. |

FOREIGN PATENT DOCUMENTS

| | | |
|---|---|---|
| JP | H01238859 A | 9/1989 |
| JP | H04297257 A | 10/1992 |
| WO | 2013134638 A1 | 9/2013 |
| WO | 2014117128 A1 | 7/2014 |

OTHER PUBLICATIONS

Extended European Search Report, European Application No. 19200203.8, completed Nov. 20, 2019, (7 pages).

* cited by examiner

US 11,367,535 B2

PATIENT CARE SYSTEM FOR A HOME ENVIRONMENT

PRIORITY CLAIM

This application claims priority under 35 U.S.C. § 119(e) to U.S. Provisional Application No. 62/739,334, filed Sep. 30, 2018, which is expressly incorporated by reference herein.

TECHNICAL FIELD

The present disclosure is related to a healthcare communication system for use in a home of a patient. More specifically, the present disclosure is related to a healthcare communication system for use in a patient's home having a patient care hub and a deployable sensor system that is technologically agnostic and configured to provide remote patient monitoring by a caregiver when the patient is located outside of a healthcare facility (e.g., a patient's home).

BACKGROUND

A prominent concern in the healthcare field includes the limited number of available healthcare facilities (e.g., hospitals, nursing homes) offering long-term caregiver assistance due to the limited number of caregivers, the growing number of patients, and the increasing costs. Additionally, patients are often kept at healthcare facilities for extended periods of time due to the need for caregiver observation and access to a healthcare facility's communication system. The healthcare facility's communication system provides instant communication between patients, caregivers, and dispatchers. The communication system also assists caregivers by allowing for the monitoring of patients from a nurse station or other central location of the facility. Commonly, the monitored patients are required to be positioned on patient support apparatuses located within the facility in order to be kept under the observation of a caregiver via the healthcare facility's communication system. An in-home patient care system would permit the patient to return home from the healthcare facility while maintaining communication with and/or observation by the caregiver.

However, in-home patient care arrangements provide unique challenges for caregivers as in-home patient care systems are not compatible with various platforms and/or operating systems. An agnostic in-home patient care system would enable the caregiver to setup and utilize the system in most any patient care environment. This would significantly lower the cost to the patients and contribute to increased caregiver efficiency. An additional challenge is the limited ability of caregiver's to make visits to a patient's home. Caregivers often only make periodic visits to a patient's home, so when a health and/or an equipment issue arises, the patient must contact the caregiver by telephone to alert her/him/them of such problems. These issues may not always be able to be resolved over the telephone, and the resolution may be delayed until the next scheduled visit unless the caregiver makes an unscheduled trip to the patient's home. Additionally, a health or equipment issue(s) may go unnoticed by the patient such that the caregiver is not aware of the issue until the next in-home visit. An in-home patient care system configured to be in electronic communication with a caregiver controller would enable the notification of caregivers to a health and/or equipment issue without requiring that the patient contact the caregiver. Further, a controller configured to allow a caregiver to alter the state of the patient located on the patient support apparatus without the caregiver returning to the patient's home or waiting until the next scheduled visit to alter the state of the patient would provide care at a reduced expense.

SUMMARY

The present disclosure includes one or more of the features recited in the appended claims and/or the following features which, alone or in any combination, may comprise patentable subject matter.

In a first aspect of the present disclosure, a patient care system includes a deployable sensor system including an at least one sensor configured to monitor a patient and wirelessly communicate a plurality of sensed data. A patient care hub is configured to receive the plurality of sensed data from the at least one sensor, discern patient activity, monitor the sensed data, and wirelessly communicate the sensed data and discerned activity of the patient. A patient interface is configured to communicate wirelessly with the patient care hub.

In some embodiments of the first aspect, the patient care system further comprises a caregiver controller configured to wirelessly communicate with the patient care hub and the patient interface.

In some embodiments of the first aspect, the at least one sensor is removeably coupled to a patient support apparatus and is configured to monitor the physiological parameters of the patient, and wirelessly communicate with the patient care hub.

In some embodiments of the first aspect, the patient care hub is further configured to be operable with a variety of sensors such that the variety of sensors are interchangeable with the at least one sensor of the deployable sensor system.

In some embodiments of the first aspect, the patient care hub is further configured to generate a risk score and a change in status score. The risk score represents how likely a patient is to degenerate, and the change in status score represents the status of patient progress or degeneration.

In some embodiments of the first aspect, the patient interface and the caregiver controller includes a microphone and a speaker. The patient interface and the caregiver controller are further configured to provide voice communication between the patient and a caregiver.

In some embodiments of the first aspect, the patient interface is configured to communicate wirelessly with a caregiver entry system. The caregiver entry system is configured to unlock a patient's home in response to an unlock command input into the patient interface by the patient.

In some embodiments of the first aspect, the patient interface further includes a visual display configured to display communications from the patient care hub and the caregiver controller.

In some embodiments of the first aspect, the visual display is further configured to display a progress measure and a motivational message.

In some embodiments of the first aspect, the patient interface is coupled to a patient support apparatus via a locking mechanism removeably coupled to the patient interface and the patient support apparatus. The locking mechanism is configured to maintain the coupling of the patient interface and the patient support apparatus until the locking mechanism is released by the caregiver.

In some embodiments of the first aspect, the patient interface is electronically coupled to the patient care system and configured to communicate an alert to the caregiver when the patient interface is electronically uncoupled from the patient care system.

In some embodiments of the first aspect, the patient care system further comprises an at-home positioning system configured to communicate wirelessly with the caregiver controller and operable to receive a plurality of instructions from the caregiver controller, react to the plurality of instructions, and monitor the at-home positioning system for compliance with the plurality of instructions.

In some embodiments of the first aspect, the caregiver controller is configured to be remotely located such that the caregiver controller and the patient care hub are separated by at least a distance.

In a second aspect of the present disclosure, the patient care system includes a deployable sensor system including an at least one sensor configured to monitor a patient and wirelessly communicate a plurality of sensed data. A patient care hub is configured to receive the plurality of sensed data from the at least one sensor, discern patient activity, monitor the sensed data, and wirelessly communicate the sensed data and discerned activity of the patient. A patient interface is configured to communicate wirelessly with the patient care hub. A caregiver controller is configured to communicate wirelessly with the patient care hub and the patient interface.

In some embodiments of the second aspect, the patient care system further includes an at-home positioning system configured to communicate wirelessly with the caregiver controller and operable to adjust the patient supported on a patient support apparatus. At least one inflatable bladder is positioned to provide support for the patient when the patient is positioned on at least a portion of the patient support apparatus. A pressure-control assembly is operably coupled to the at least one inflatable bladder and configured to regulate a pressure within the at least one inflatable bladder. The pressure-control assembly includes a programmable controller configured to communicate wirelessly with the caregiver controller and operable to monitor a sensed pressure value of a fluid pressure within the at least one inflatable bladder and adjust the fluid pressure within the at least one inflatable bladder in response to a plurality of instructions from the caregiver controller.

In some embodiments of the second aspect, the programmable controller is further configured to communicate wirelessly with the deployable sensor system, receive a plurality of sensed data from the sensor system, discern a patient health status, compare the patient health status to At least one predefined parameter, and communicate an alert to the caregiver controller when the patient health status violates one of the at least one predefined parameters.

In some embodiments of the second aspect, the at-home positioning system is configured to be remotely activated by the caregiver controller. The caregiver controller is configured to wirelessly communicate with a bladder controller configured to activate a pump. The pump is configured to direct a flow of air towards the at least one inflatable bladder.

In some embodiments of the second aspect, the at-home positioning system further includes an angle sensor coupled to the at least one inflatable bladder and configured to wirelessly communicate an angle of the at least one inflatable bladder to the programmable controller. The bladder controller is further configured to communicate with a pressure control valve configured to control a flow of air and change the angle of the at least one inflatable bladder.

In some embodiments of the second aspect, the bladder controller is further configured to communicate wirelessly with the deployable sensor system, receive a plurality of signals from the sensor system, discern a patient health status, compare the patient health status to an at least one predefined parameter, and automatically adjust the at least one inflatable bladder in response to a violation of one of the at least one predefined parameters.

In some embodiments of the second aspect, the at least one sensor is configured to measure an oxygen saturation level of the patient. The bladder controller is further configured to increase the angle of the at least one inflatable bladder positioned under a head section of the patient support apparatus to at least 30° in relation to a seat section of the patient support apparatus in response to an oxygen saturation level of less than 90%.

In some embodiments of the second aspect, the bladder controller is configured to increase an angle of at least one inflatable bladder positioned under a head section of the patient support apparatus to at least 45° in relation to the seat section of the patient support apparatus in response to an oxygen saturation level of less than 90%.

In some embodiments of the second aspect, the bladder controller is configured to wirelessly communicate with the caregiver controller in response to an oxygen saturation level of less than 90% after increasing the angle of the at least one inflatable bladder positioned under a head section of the patient support apparatus to at least 45° relative to the seat section of the patient support apparatus.

In a third aspect of the present disclosure, the patient care system includes a deployable sensor system including an at least one sensor. A patient care hub is configured to receive a plurality of signals from the at least one sensor and wirelessly communicate the plurality of signals. A patient interface is configured to communicate wirelessly with the patient care hub. A caregiver controller is configured to communicate wirelessly with the patient care hub and the patient interface.

In some embodiments of the third aspect, the at least one sensor is configured to be physically engaged with a patient assistance device, a patient, the patient care hub, a patient support apparatus, or some combination thereof.

In some embodiments of the third aspect, the patient care hub is configured to compare a first signal from an at least one sensor physically engaged with the patient and a second signal from an at least one sensor physically engaged with the patient assistance device to determine patient adherence to a prescribed care plan. The patient care hub is further configured to communicate an alert to the caregiver controller if the first signal and the second signal are not simultaneously active.

In some embodiments of the third aspect, the patient care hub is configured to automatically update a patient's priority and recommend changes to a caregiver's schedule stored in the caregiver controller in response to a change in a risk score of the patient.

In some embodiments of the third aspect, the patient care hub is further configured to monitor, track, and communicate a historical data of patient activity and caregiver interaction with the patient.

In some embodiments of the third aspect, the patient care system further includes a patient monitoring system in communication with the sensor system and configured to receive an at least one signal from the sensor system relating to patient movement.

In some embodiments of the third aspect, the patient monitoring system is configured to wirelessly communicate with the caregiver controller and includes a transmitter removeably coupled to the patient support apparatus, a receiver configured to wirelessly communicate with the transmitter and removeably coupled to a patient, and a plurality of wiring configured to create a first zone between a first point and a second point and a second zone extending from the second point outwardly away from the patient support apparatus.

In some embodiments of the third aspect, the patient monitoring system is configured to monitor patient movement in the first zone and the second zone and communicate the location of patient movement relative to the first zone and the second zone to the caregiver controller.

In some embodiments of the third aspect, the patient interface is further configured to activate the patient care system and wirelessly communicate an identity of a patient. The patient care system is configured to access a patient's medical history and a caretaker's orders in response to the confirmation of the patient's identity.

In some embodiments of the third aspect, the patient interface enables the patient care system to associate the identity of the patient with the particular patient care system such that a plurality of patient data from the associated care system is communicated to the patient care hub and the caregiver controller. The plurality of patient data containing the identity of the patient using the patient care system.

Additional features, which alone or in combination with any other feature(s), such as those listed above and/or those listed in the claims, can comprise patentable subject matter and will become apparent to those skilled in the art upon consideration of the following detailed description of various embodiments exemplifying the best mode of carrying out the embodiments as presently perceived.

BRIEF DESCRIPTION OF THE DRAWINGS
START HERE

The detailed description particularly refers to the accompanying figures in which.

DETAILED DESCRIPTION

Figure 1:
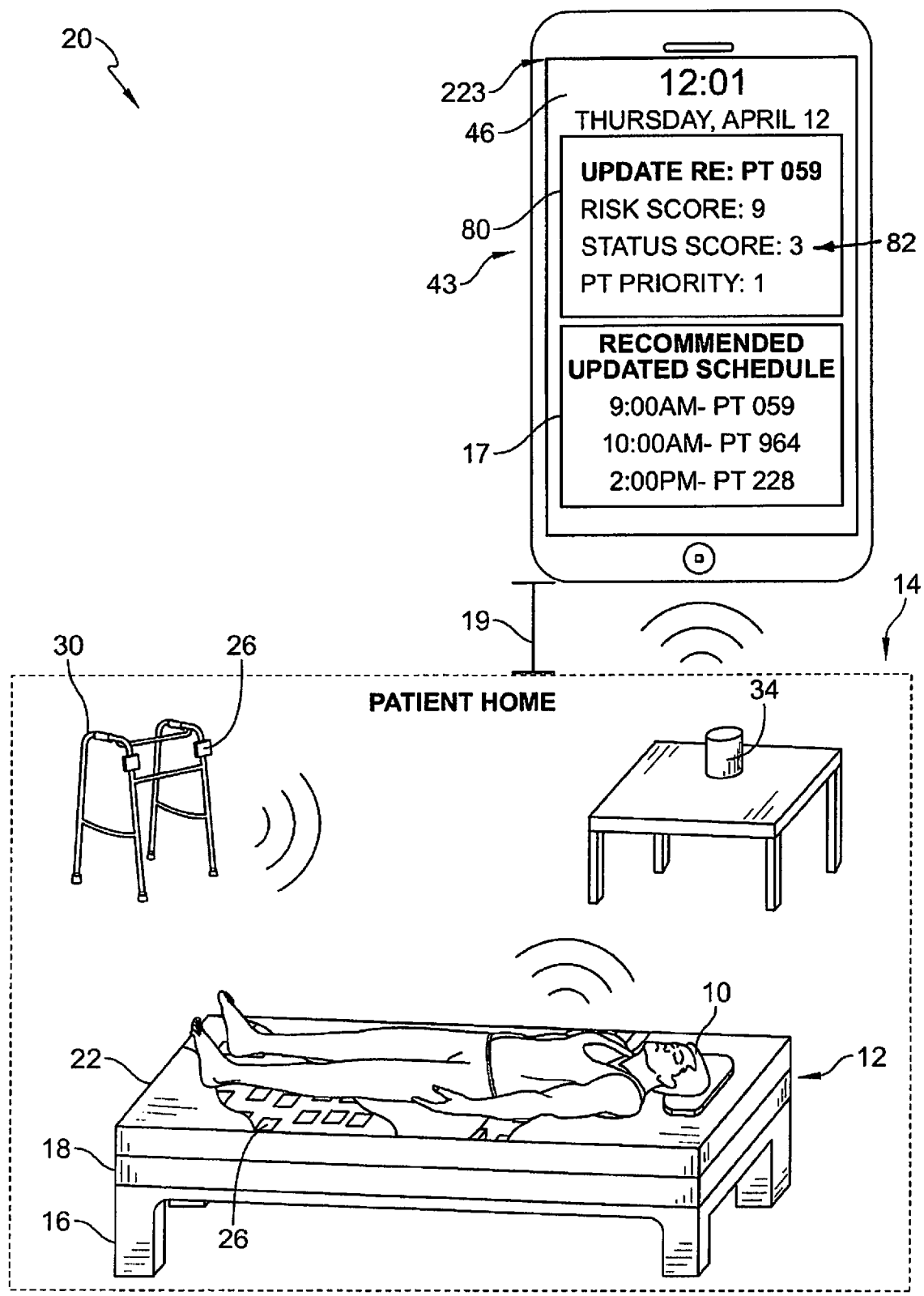
FIG. 1 is a diagrammatic view showing a patient care system in a patient's home and a caregiver controller located outside of the patient's home and in wireless communication with the patient care system.

A patient care system 20 in accordance with the present disclosure is adapted for use with a patient support apparatus 12 such as, for example, a patient's personal bed located in their home as shown in FIG. 1. Illustratively, the patient care system 20 is independent of the patient support apparatus 12.

The patient care system 20 is configured to removably couple to the patient support apparatus 12, monitor physiological factors of the patient 10 that affect the patient's health to evaluate what response, if any, is appropriate upon detecting or predicting the occurrence of pre-programmed conditions, communicate information to a caregiver 24, receive and complete care plan instructions remotely input by the caregiver 24, and allow for communication between the caregiver 24 and the patient 10.

Because the patient care system 20 is removable, the patient care system 20 may be used with varied patient support apparatuses 12 and may be obtained as an aftermarket accessory separate from the patient support apparatus 12. As a result, the patient care system 20 may be coupled to a variety of embodiments of the patient support apparatus 12 such as a chair, a wheelchair, a table, a gurney, a stretcher, or the like. In addition, the patient care system 20 is configured to be used with a variety of software platforms and operating systems further enabling the transferability of the patient care system 20 between patient homes.

Referring to FIG. 1, a patient 10 is shown positioned on a patient support apparatus 12 illustratively embodied as a home bed located in a patient's home 14. The patient support apparatus 12 may include a frame 16, a base 18, and a patient support surface 22. In some embodiments, the patient support surface 22 is moveable in relation to the frame 16 between a plurality of positions. FIG. 1 further shows a patient care system 20 according to one contemplated embodiment. The system 20 is configured to further determine whether to implement an intervention to address the patient's physiological factors measured by the system 20 to avoid a decline in patient health and enable communication between the patient 10 and a caregiver 24. The physiological factors that the system 20 is configured to measure include, but are not limited to, presence of an infection at a surgical site or chronic wound, blood pressure, temperature, respiratory rate, heart rate, peripheral capillary oxygen saturation (SpO2), patient movement, time elapsed since the last caregiver visit and/or vital check, type of intervention used by the caregiver 24, historical data of patient activity and patient-caregiver interaction, time elapsed between a patient call and a caregiver response, location of the patient, the angle to which one or more elements of the patient support surface 22 is adjusted, blood glucose level of the patient, patient nutrition, patient hydration, and movement of a patient assistance device 30. The system 20 is further configured to associate various factors in order to determine the health of the patient 10. Such factors may include patient 10 adherence to a prescribed respiratory therapy, patient 10 medication compliance, and/or patient 10 adherence to a prescribed physical therapy. The system 20 is configured to either periodically or continuously monitor such factors. In some embodiments, the system 20 may be configured to alternate between periodic monitoring and continuous monitoring so that the caregiver 24 may switch between the two monitoring modes.

The patient care system 20 may be in communication with an emergency medical record (EMR) or other care facility record or database system and configured to receive information necessary to determine the patient's risk for declining health or other factors that would influence the caregiver's treatment decision. In one example, the system 20 receives information from the EMR including, but not limited to, the patient's medical history, medical diagnosis, current medications, Braden score, and risk analyses. In another example, the system 20 receives information from the institutional system protocols including, but not limited to, a compliance protocol, a safety protocol, a theft prevention protocol, a fall prevention protocol, an entrance unlock protocol, and an oxygen saturation protocol. The aforementioned protocols may include information concerning care procedures. Each protocol is discussed in further detail below.

The system 20 is configured to respond to measured factors that exceed a predetermined threshold by activating a programmed therapy or notifying the caregiver 24 and requesting that the caregiver 24 perform an action(s), such as, repositioning at least a portion of the patient 10 or actuating a care protocol(s). The system 20 is also configured to provide information to the EMR or other care facility database or record system for compliance reporting and charting, as discussed above. The system 20 is configured to remotely update a caregiver 24 with patient information and allow for the caregiver 24 to respond to this information. Upon notifying the caregiver 24, the system 20 is configured to receive a command from the caregiver 24 via the caregiver controller 43. The command instructs the system 20 of its next steps regarding the patient's care, including, but not limited, to providing a multitude of therapies, moving the patient 10, measuring the patient's vitals, and/or communicating with the patient 10 located on the patient support apparatus 12.

Illustratively, the patient support apparatus 12 is the patient's personal bed located in the patient's home 14. The patient support apparatus 12 may include the frame 16, the base 18 positioned on top of and in close relation to the frame 16, and the patient support surface 22 moveably supported above and spaced apart from the frame 16 by the base 18. Illustratively, the patient support surface 22 is embodied as a mattress, as shown in FIG. 1. The patient support surface 22 is configured to move independent of the frame 16 and the base 18 with respect to the frame 16. The patient support surface 22 is further configured to move between various orientations, such as, but is not limited to, a High Fowler's position, a Fowler's position, and a Semi Fowler's position as shown in FIG. 13.

Figure 13:
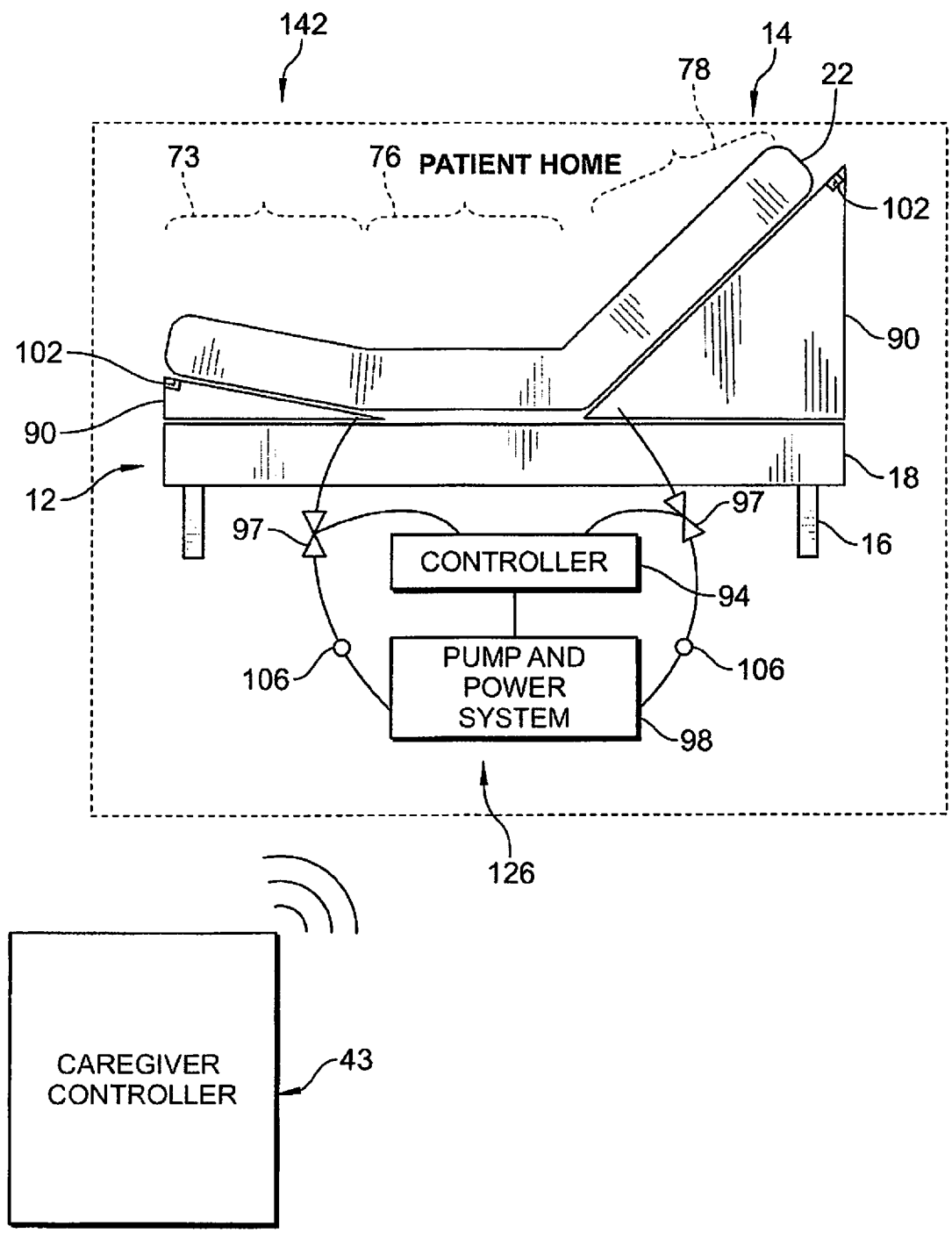
FIG. 13 is a partial diagrammatic and schematic view similar to FIG. 12 showing a first inflatable bladder of the remote positioning system positioned under a head section of the mattress and a second inflatable bladder of the remote positioning system positioned under a foot section of a mattress of the patient support apparatus.

The patient support surface 22 further includes a foot section 73, a seat section 76, and a head section 78 as shown in FIG. 13. The head section 78 and the foot section 73 are movable relative to the seat section 76 and/or the frame 16. In some contemplated embodiments, the foot section 73, the seat section 76, and the head section 78 cooperate to move the patient support apparatus 12 between a substantially planar or lying down configuration and a Fowler's position. In some contemplated embodiments, the foot section 73, the seat section 76, and the head section 78 cooperate to move the patient support apparatus 12 between a substantially planar or lying down configuration and an angled or reclined positon. In some contemplated embodiments, the foot section 73 is movable independent of the head section 78 with respect to the seat section 76.

Figure 2:
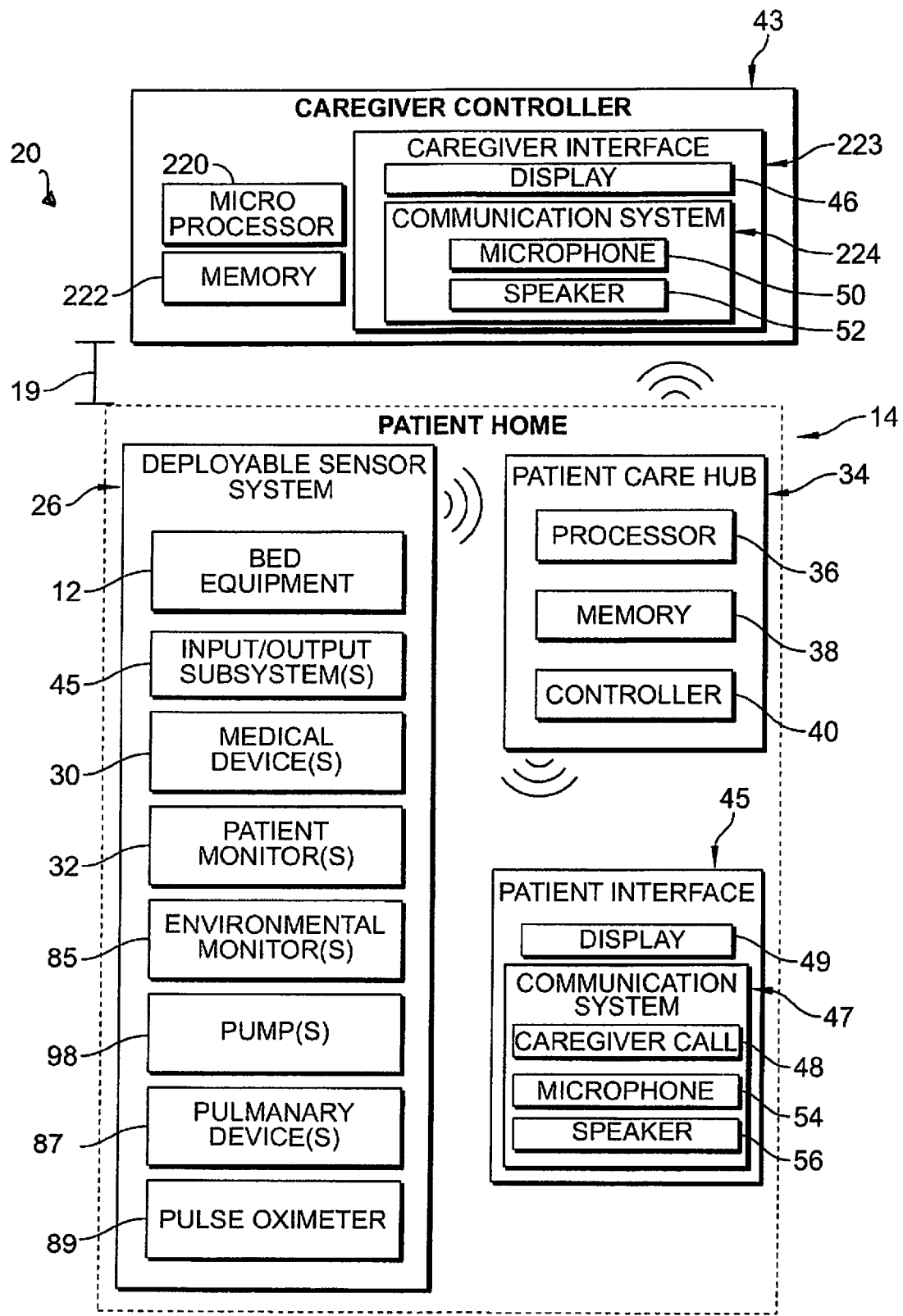
FIG. 2 is a diagrammatic view showing the communicative relationships between the caregiver controller, a patient care hub, a deployable sensor system, and a patient interface.

The system 20 includes a deployable sensor system 26, a patient care hub 34, and a caregiver controller 43 as shown in FIGS. 1 and 2. The deployable sensor system 26 includes at least one sensor 26 configured to wirelessly communicate with the patient care hub 34. The patient care hub 34 includes a microprocessor 36, a memory 38, and a controller 40 and is configured to assess and respond to adverse conditions that are detected by the sensor system 26. The caregiver controller 43 includes a microprocessor 220, a memory 222, and a communication system 224 and is configured to wirelessly communicate with the patient care hub 34 and a patient interface 45, as shown in FIG. 2. The patient care system 20 is configured to be used with the patient support apparatus 12 as further discussed below.

As shown diagrammatically in FIG. 2, the deployable sensor system 26 is agnostic and may be coupled to a variety of elements such as bed equipment 12, an input/output subsystem(s) 45, the patient assistance device(s) 30, a patient monitor(s) 32, an environmental monitor(s) 85, a pump(s) 98, a pulmonary device(s) 87, a pulse oximeter(s) 89, and other medical devices known to one skilled in the art. The sensor system 26 is configured to wirelessly communicate with the patient care hub 34 and provide input to the patient care hub 34 concerning sensed data about the patient 10 and the environment indicative of the status of a therapy, the identity of the patient 10 located on the patient support apparatus 12 coupled to the patient care system 20, and/or a characteristic of the patient 10, such as, the patient's heart rate, respiration rate, respiration amplitude, skin temperature, weight, sleep state, body orientation, current physical position, and/or other physiological characteristics or information about the patient's condition. In some contemplated embodiments, the sensor system 26 may include temperature sensors, force sensors, pressure sensors, moisture sensors, and ultrasonic sensors that are positioned on top of and removeably coupled to the patient support surface 22. In some contemplated embodiments, the sensor system 26 may include accelerometer sensors and piezoelectric sensors that are coupled to garments, linens, and/or the patient's skin. In some contemplated embodiments, force sensors and video sensors are removeably coupled to the patient support apparatus. In some contemplated embodiments, video sensors are positioned in the patient's home 14 and positioned to observe the patient 10. In some contemplated embodiments, some of the sensors of the sensor system 26 are incorporated into a topper positioned on top of the person support surface 22, for example, as disclosed in U.S. Pat. No. 7,515,059 to Price et al., U.S. Patent Publication No. 2011/0068928 to Riley et al., and U.S. Patent Publication No. 2011/0024076 to Lachenbruch, et al. In some contemplated embodiments, the sensors are load cells removeably coupled to the frame 16. The sensors of the sensor system 26 are further configured to removeably couple to the person support apparatus 12, integrate into linens or garments and/or underpads, and/or removeably coupled to the patient 10. The sensor system 26 is configured to wirelessly connect to the system 20 to allow the sensors to convey the sensed data as output to the patient care hub 34.

The patient care hub 34 is configured to assess and respond to adverse conditions detected by the sensors of the sensor system 26 or conveyed by caregiver 24 via the caregiver controller 43, the patient interface 45, or other communication means. The patient care hub 34 is further enabled to run a variety of algorithms concerning the monitoring of a variety of patient data and configured to wirelessly couple to and communicate with a variety of sensors of the sensor system 26 simultaneously to best monitor the patient 10. Illustratively, the algorithms programmed into the patient care hub 34 are configured to communicate motivation factors to the patient 10, associate the identity of the patient 10 with a patient interface 45 assigned to the patient 10 to pre-populate the patient interface 45 and/or the caregiver controller 43, and/or determine the location of the patient interface 45 and alert the caregiver 24 when the location cannot be determined. In illustrative embodiments, the algorithms programmed into the patient care hub 34 are further configured to determine the present oxygen saturation level of the patient 10 and instruct an at-home positioning system 88 to adjust the patient support apparatus 12 and/or alert the caregiver 24, determine the present location of the patient 10 and communicate the location of the patient 10 to the caregiver 24, determine the probability of completion of care by a patient 10, and communicate with an entrance to the patient's home to remotely unlock the entrance to the patient's home. In additional illustrative embodiments, the algorithms are further configured to monitor the patient 10, enable caregiver 24 and patient 10 communications, and determine changes in the patient's health.

Figure 3:
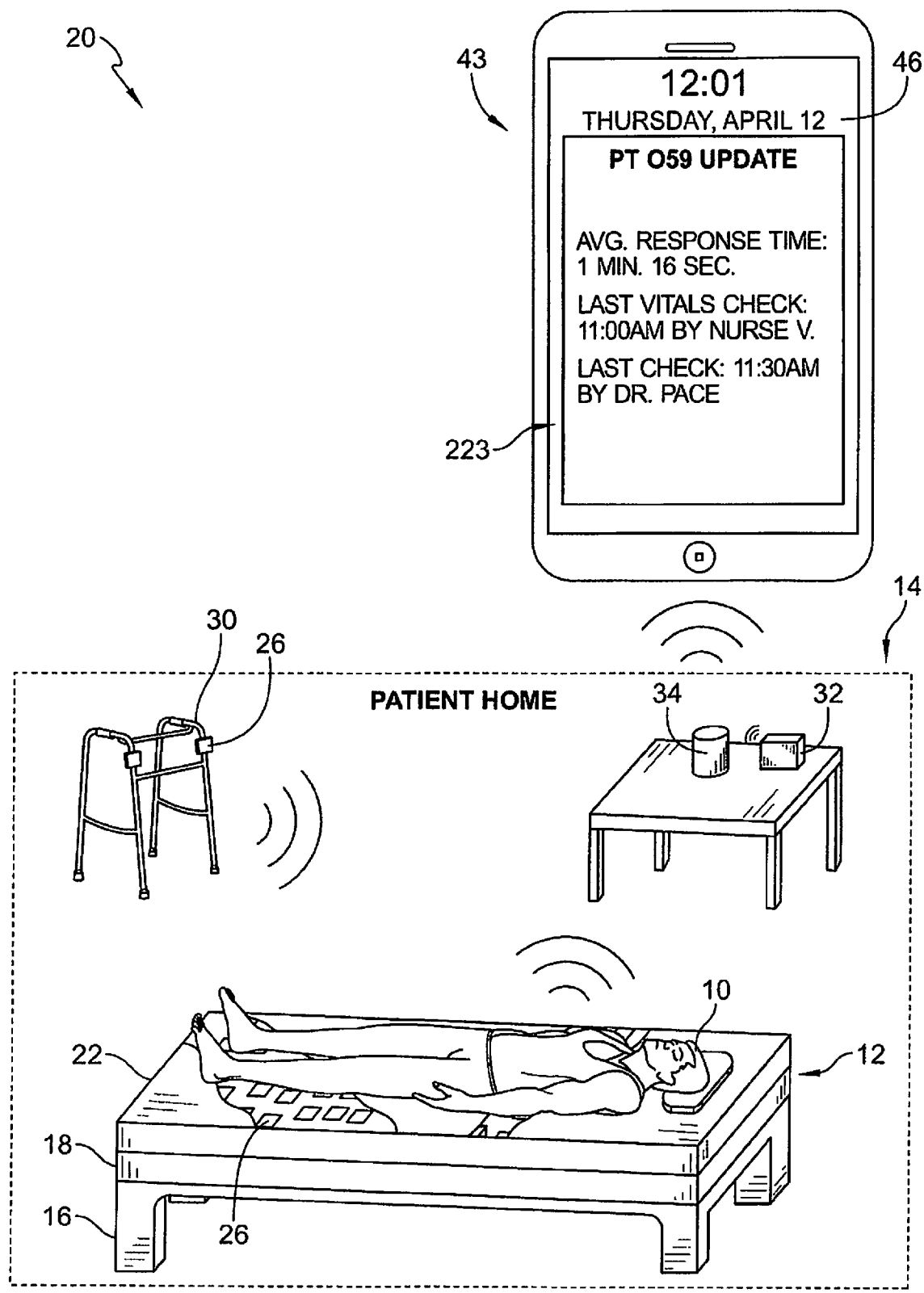
FIG. 3 is a diagrammatic view showing the patient care hub of the patient care system in communication with a vitals monitor.

Illustratively, the patient care hub 34 is positioned in close proximity to the patient support apparatus 12 located within the patient's home 14 and is configured to wirelessly communicate with the caregiver controller 43 as shown in FIGS. 1-3. The patient care hub 34 is further configured to wirelessly communicate with the caregiver controller 43 when the caregiver controller 43 is located outside of the patient's home 14. This allows the caregiver 24 to communicate with the patient 10 as well as receive updates and/or alerts from the patient care system 20. Further, the patient care hub 34 may be used with a variety of software platforms and operating systems such that patient care hub 34 is moveable between patient homes 14 and configured to communicate with a variety of deployable sensor systems 26 and caregiver controllers 43. Illustratively, the system 20 is agnostic.

The patient care hub 34 includes a microprocessor 36, a memory device 38, and a controller 40 as shown in FIG. 2. The patient care hub 34 is configured to receive at least one input. In contemplated embodiments, the input 68 is provided by the sensors of the sensor system 26 configured to wirelessly communicate patient data and environmental information to the microprocessor 36 of the patient care hub 34. In additional contemplated embodiments, the input 68 is provided by the patient 10 via the patient interface 45. In other contemplated embodiments, the input 68 is provided from a remote database or system, such as, an electronic medical record (EMR) system or care facility record or information databases, in wireless communication with the microprocessor 36. In some contemplated embodiments, the information provided by the input 68 includes, but is not limited to, risk assessments of the patient 10, a patient's medical history, the patient's medications, the patient's Braden scores, health conditions of the patient 10, the patient's nutritional information, assessed sensory perception information of the patient 10, staffing levels of the facility, care facility standard protocols, caregiver alarm preferences, agitation level of the patient 10, and other information related to the patient 10, the caregiver 24, and/or the care facility. In some contemplated embodiments, the microprocessor 36 is configured to output information, automatically or manually by the caregiver 24, to the EMR for charting. This output may include therapy initiation and termination, adverse event occurrence information, therapy protocol(s) used, caregiver ID, and any other information associated with the patient 10, the caregiver 24, the patient support apparatus 12, the person support surface 22, and/or adverse events related to the patient 10.

The microprocessor 36 of the patient care hub 34 is configured to receive an input(s) 68. The input(s) 68 provide patient and environmental information that may include both spatial and temporal components and may relate to a variety of information, including, but not limited to, the patient's current diagnosis, the patient's medications, the patient's physiological characteristics, the patient's medical history, risk assessments performed by the caregiver 24, medical procedures the patient 10 has undergone, the status of medical equipment and patient assistance devices 30 in the vicinity of the patient 10 or that are associated with the patient 10 (i.e., the person support apparatus 12 and the person support surface 22), care facility protocols and procedures, care facility logistics, and other information about the patient 10, the patient assistance device(s) 30, the caregiver 24, and/or the care facility that can be provided by an EMR or a patient activity log. The patient activity log is gathered by and from the patient support apparatus 12 and mattress 22 and other patient assistance devices 30 assigned to the patient 10.

The memory 38 of the patient care hub 34 is configured to store, amongst other things, instructions in the form of, for example, a software routine(s) which, when executed by the microprocessor 36, allow the patient care hub 34 to control operation of the features of the patient support apparatus 12 when the patient care system 20 is armed. The memory device 38 may be, for example, a programmable read-only memory device ("PROM") including erasable PROM's (EPROM's or EEPROM's). In some contemplated embodiments, the system 20 is armed manually by the caregiver 24 or automatically based on information from the patient's EMR, the caregiver 24, and/or a protocol triggered by the risk profile of the patient 10. After the patient care system 20 is armed, the instruction sets of the protocols define procedures that cause the microprocessor 36 to implement one or more protocols. Such protocols may include, but are not limited to, wirelessly alerting the caregiver 24 when the system 20 detects that a programmed threshold has been violated so that the caregiver 24 may manually input care instructions regarding the patient 10 or the patient care system 20 may automatically run one or more therapies in response to the patient 10 exceeding a programmed threshold.

Figure 14:
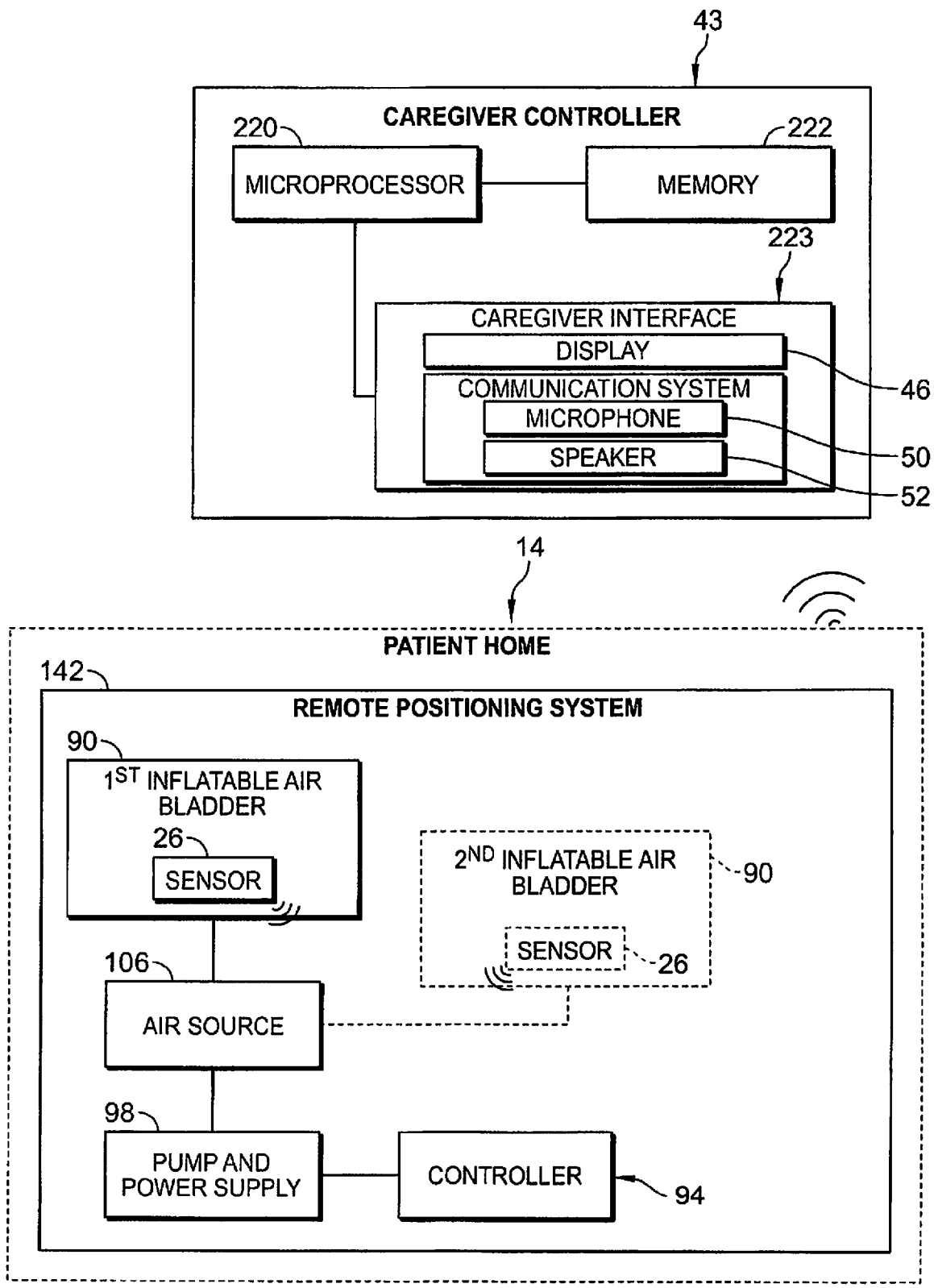
FIG. 14 is a diagrammatic view similar to FIGS. 12 and 13 showing the communicative relationships within the caregiver controller and the communicative relationship between the angle sensors and the bladder controller showing that the bladder controller is configured to wirelessly communicate with the angle sensors and the caregiver controller.

The caregiver controller 43 is illustratively shown as a cellular phone in FIG. 1, but any electronic device may be used. The caregiver controller 43 is configured such that a caregiver 24 may remotely communicate with the patient care hub 34 and/or the patient 10 when the caregiver controller 43 is spaced apart from the patient care hub 34 a distance 19. The caregiver controller 43 includes a microprocessor 220, a memory 222, and a caregiver interface 223 as shown in FIGS. 2 and 14. The microprocessor 220 of the caregiver controller 43 is configured to receive inputs from the caregiver 24 regarding the patient's health, the patient's care plan, commands to the patient care hub 34, as well as other information regarding the patient 10. The memory 222 is configured store, amongst other things, instructions in the form of, for example, a software routine(s) which, when executed by the microprocessor 220, allow the caregiver controller 43 to communicate with the patient care hub 34 regarding the control operation of the patient support apparatus 12 when the patient care system 20 is armed. Illustratively, the caregiver interface 223 includes a display screen 46 and a communication system 224. The display screen 46 is operable to generate or display a graphical user interface (GUI) to enable the user to interface with components of the patient support apparatus 12 to control one or more features of the patient support apparatus 12. The display screen 46 is a touchscreen capable of generating input data in response to being touched by the user 24, illustratively. The communication system 224 includes a microphone 50 and a speaker 52 and is configured to communicate with the patient interface 45 and/or the patient care hub 34. The caregiver controller 43 may further include a plurality of hard buttons. The caregiver controller 43 is configured to wirelessly communicate information to the caregiver 24 and allow a caregiver to remotely control various functions of the patient support apparatus 12.

Figure 6:
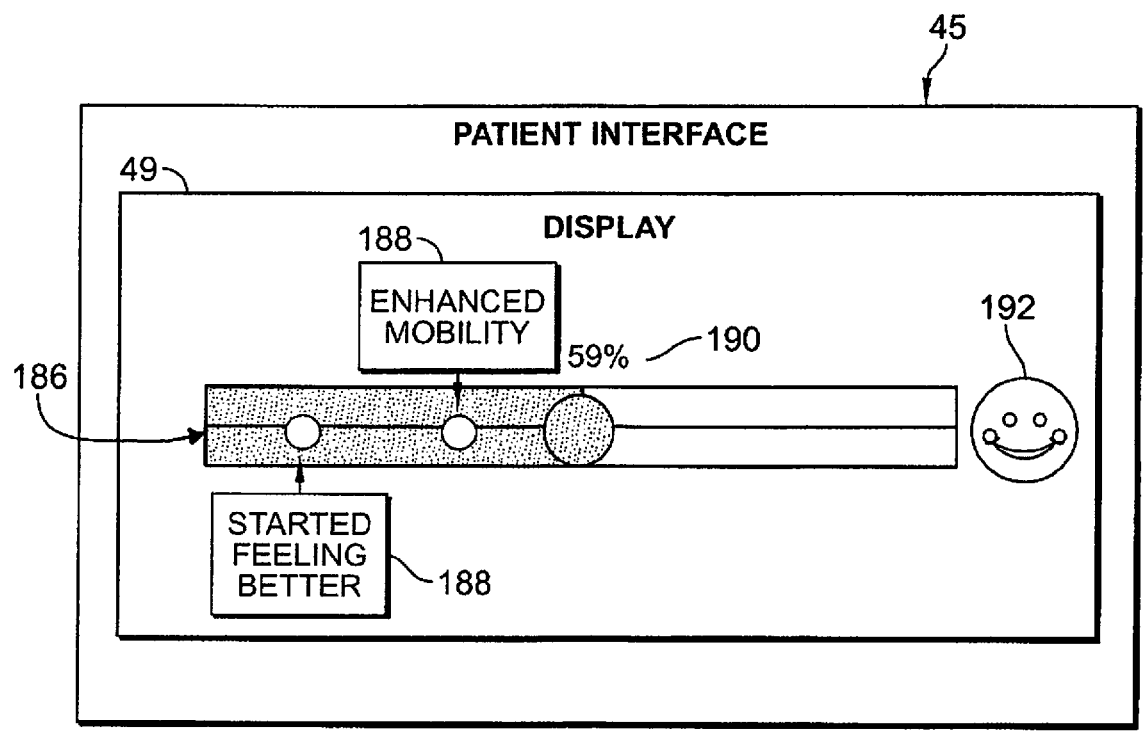
FIG. 6 is a diagrammatic view of an illustrative embodiment of the patient interface showing a progress bar with health markers identifying significant events, a percentage of completion, and various events concerning a patient's care plan.

In illustrative embodiments, the system 20 includes two user input devices 188 as shown in FIG. 6. The second user input is a patient interface 45. The patient interface 45 is electronically coupled to the patient care hub 34 and the caregiver controller 43 and is capable of receiving inputs from a user (e.g., a patient, hospital staff, caregiver, etc.) 24. The patient interface 45 includes a display 49 and a communication system 47 configured to wirelessly communicate with the patient care hub 34 and the caregiver controller 43. The communication system 47 includes a microphone 54, a speaker 56, and a caregiver call 48. In some embodiments, the communication system 47 may further include a camera that is capable of providing a caregiver a view of the patient from a remote location. Further, in embodiments of the system 20 in which the inputs are shown on a graphical display, the system 20 is also capable of providing output to the user 24 related to various sensed and/or configuration data of the patient support apparatus 12. Sensed data may include various sensor readings related to current positions, levels, temperatures, pressure levels, etc. of various components of the patient support apparatus 12. In some embodiments, the configuration data may include various settings for positioning the components of the patient support apparatus 12 (e.g., a designated angle of the head section 78 of the patient support apparatus 12 relative to the seat section 76 or the bed frame 16), notifications based on detected events corresponding to the sensed data, and/or any other configurable data that may be set by the user 24 and managed by the patient care hub 34.

Figure 7:
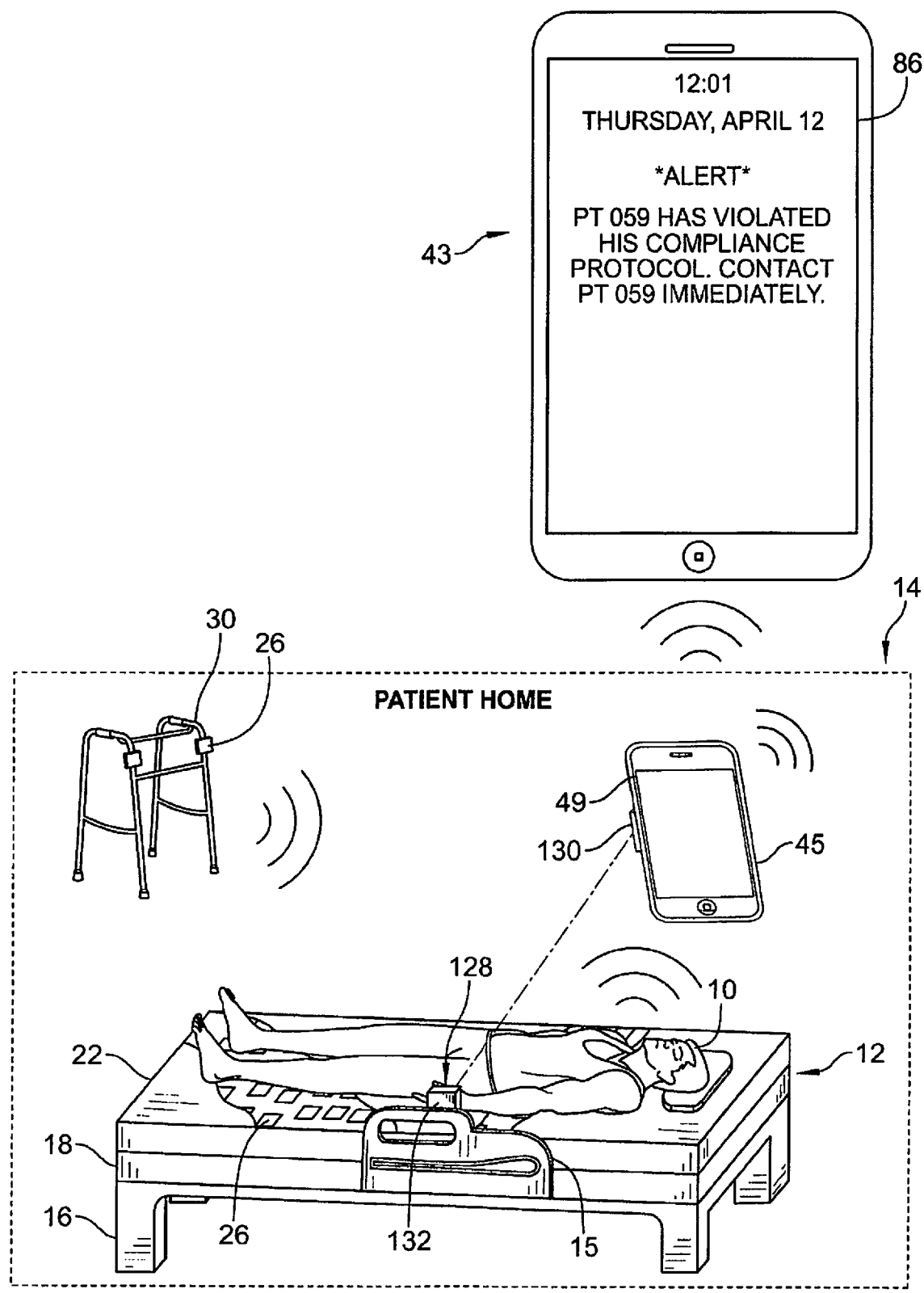
FIG. 7 is a side elevation view of an illustrative embodiment of the patient care hub showing the patient care hub exploded from a siderail removeably coupled to a patient support apparatus.

As shown in FIG. 7, the patient interface 45 is configured to couple to a siderail 15 of the system 20 so that the patient 10 may access the patient interface 45. The patient interface 45 is intended to be accessible by the patient 10 supported on the patient support apparatus 12. The patient interface 45 in the illustrative embodiment a removable hand-held electronic device is mounted to the siderail 15 and facing inwardly toward the patient 10 supported on the patient support apparatus 12. As previously mentioned, the patient interface 45 has a display screen 49, a caregiver call 48, a microphone 54, and a speaker 56. The display screen 49 is operable to generate or display a graphical user interface (GUI) to enable the patient 10 to communicate with a caregiver 24. The caregiver call 48 is configured to directly connect the patient 10 to the caregiver 24 in case of a need for immediate assistance and/or an emergency.

In the illustrative embodiment of FIG. 1, the patient 10 is located on the patient support apparatus 12 in the patient's home 14. Deployable sensors of the sensor system 26 are positioned on top of the mattress 22 but may be positioned below a sheet such that they are not in contact with the patient 10. In additional embodiments, the sensors of the sensor system 26 may be directly coupled to the patient 10. An additional sensor 26 is coupled to a walker 30 located within the patient's home 14. The sensors of the sensor system 26 removeably coupled to the mattress 22 and the walker 30 are configured to communicate with the patient care hub 34 located within the patient's home 14. Illustratively, the sensors of the sensor system 26 communicate patient information and/or sensed data to the patient care hub 34 to enable the patient care hub 34 to synthesis the sensed data to determine the most efficient course of action. In some instances, the determined course of action includes communicating an alert and/or information to the caregiver controller 43 such that the caregiver 24 may act on the alert and/or information. Alternatively, the determined course of action may include an automatic response by the patient care hub 34 when a programmed threshold is exceeded or another trigger occurs.

The information communicated to the caregiver controller 43 by the patient care hub 34 may include a patient risk score 80 and/or a change in status score 82 as shown in FIG. 1. To calculate the scores 80, 82, the patient care hub 34 collects the sensed data from the sensors of the sensor system 26 periodically, continuously, or at predetermined intervals. The sensed data includes the patient's vitals including the patient's blood pressure, respiration rate, heart rate, oxygen saturation level, and contextual data such as patient activity and the type and length of the caregiver's interaction with the patient 10. In additional embodiments, the sensed data may be received from a smart bandage configured to monitor a surgical site(s) and/or chronic wound(s) to determine the presence of infection and provide an early indication of infection. Illustratively, the patient care hub collects the sensed data in real time and evaluates the trend of the patient's health using a programmed algorithm. The algorithm is configured to generate the risk score 80 to determine the patient's risk of sepsis and the change in status score 82 to determine the progress or degenerating of the patient 10. Upon calculating at least one score 80, 82, the patient care hub 34 is configured to communicate an alert/update to the caregiver 24 via the caregiver controller 43. In addition, the patient care hub 34 is configured to send alerts/updates to the caregiver 24 concerning a change in the patient priority based on the at least one score 80, 82. This allows the caregiver 24 to make an informed decision concerning his/her/their schedule 17. Further, the patient care hub 34 is configured to integrate information provided by GPS-type services to assist the caregiver 24 in scheduling a patient visit based on the time of day, the distance between the caregiver and the patient's home, and the traffic associated with that time of day and route. The patient care hub 34 may send the caregiver 24 a proposed schedule 17 determined to be the most efficient based on the score(s) 80, 82 and the traffic data. Alternatively, the caregiver 24 may allow for the patient care hub 34 to automatically update his/her/their schedule 17 based upon the aforementioned information.

Additional information concerning the historical medical data of the patient 10 may also be communicated to the caregiver controller 43 and/or the patient interface 45 by the patient care hub 34. Historical medical data of the patient 10 may include patient motion, the frequency with which a patient's vitals are checked, the consistency and length of interactions between the patient 10 and the caregiver 24, and the response time of the caregiver 24 to a patient call. To ascertain such data, the sensors of the sensor system 26 are embodied as a variety of sensor types in which the sensors of the sensor system 26 are configured to measure the relevant information and convey the data to the patient care hub 34. Illustratively, when measuring the patient's motion, the sensors of the sensor system 26 are formed as motion sensors removeably coupled to the patient support apparatus 12, the siderail 15, and/or the patient 10. Such motion sensors may include optical sensors, pressure sensors, and/or accelerometers although other sensors known to measure motion and/or result in a measurement of patient movement may also be used. Further, a vitals monitor 32 may be coupled to or in electrical communication with the patient care hub 34 such that the patient care hub 34 is configured to monitor and track how often and when the patient's vitals are taken by a caregiver 24 as shown in FIG. 3. An additional sensor 26 may be coupled to the caregiver 24 and also in electrical communication with the patient care hub 34. In illustrative embodiments, the additional sensor 26 is formed as a radio-frequency identification (RFID) sensor 26 and is configured to track which caregiver 24 interacted with the patient 10 and for how long the interaction lasted based on the proximity of the RFID sensor 26 to the patient care hub 34. The patient care hub 34 is further configured to ascertain the response time of the caregiver 24 based on the sensed data and communicate this information to the caregiver controller 43 and/or the patient interface 45. This allows for the caregiver 24, the patient 10, and the patient's family to participate in the care plan even when the patient 10 is located at home 14 and receiver alerts of any sensed changes or issues concerning the patient 10.

Figure 5:
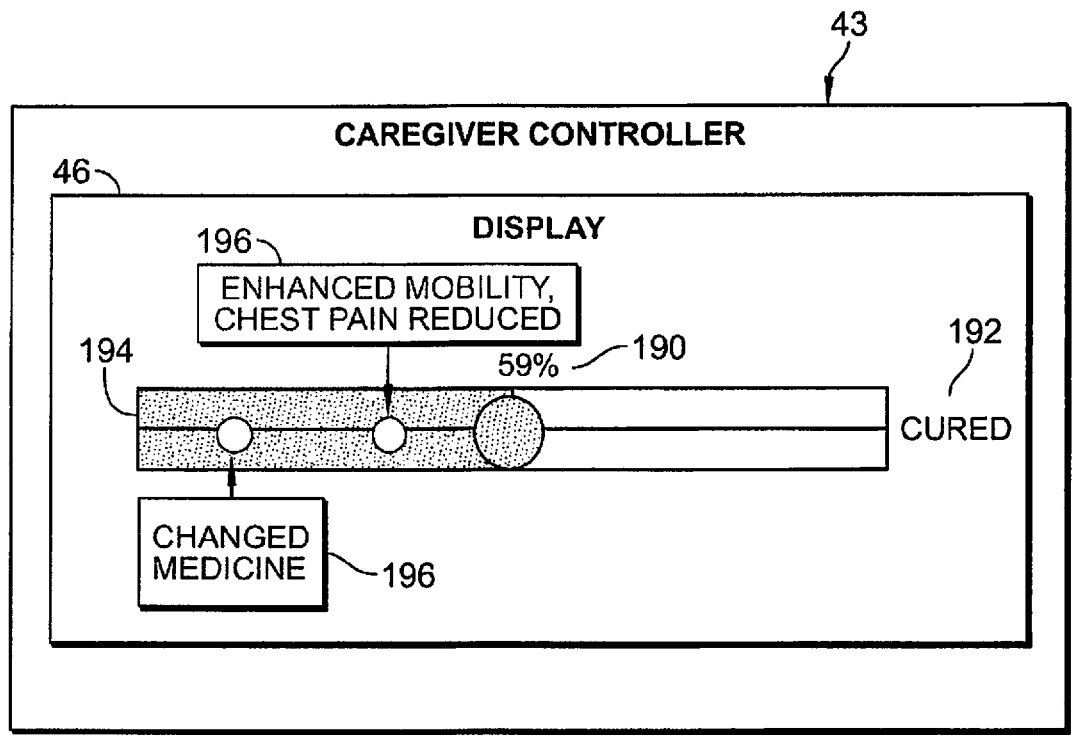
FIG. 5 is a diagrammatic view of an illustrative embodiment of the caregiver controller showing a progress bar with health markers identifying significant events, the percentage the patient is cured, and various events concerning a patient's care plan.

In some embodiments, the information provided by the sensors of the sensor system 26 to the patient care hub 34 and communicated to the caregiver controller 43 is displayed in a progress bar 194 as shown in FIG. 5. The progress bar 194 is configured to show the progress of the patient 10 in completing his/her/their treatment/care plan. The progress bar 194 may further show health markers 196 positioned on the progress bar 194 such that the caregiver 24 may identify the exact day during the patient's treatment that the patient 10 achieved an improvement. The health markers 196 may also identify when the caregiver 24 changed the patient's medicine, when the patient 10 developed increased mobility and decreased chest pain, etc. Further, a percentage of completion 190 may also be shown so that the caregiver 24 is aware of how far the patient 10 has progressed thus far. Informative labels/graphics 192 may also be used to convey the appropriate direction in which the progress bar 194 moves when the patient 10 is progressing well through his/her/their care plan and the care plan is improving the health of the patient 10. In additional contemplated embodiments of the caregiver controller display screen 46, the progress bar 194 is configured to show the daily improvements/highlights of the patient 10.

Figure 4:
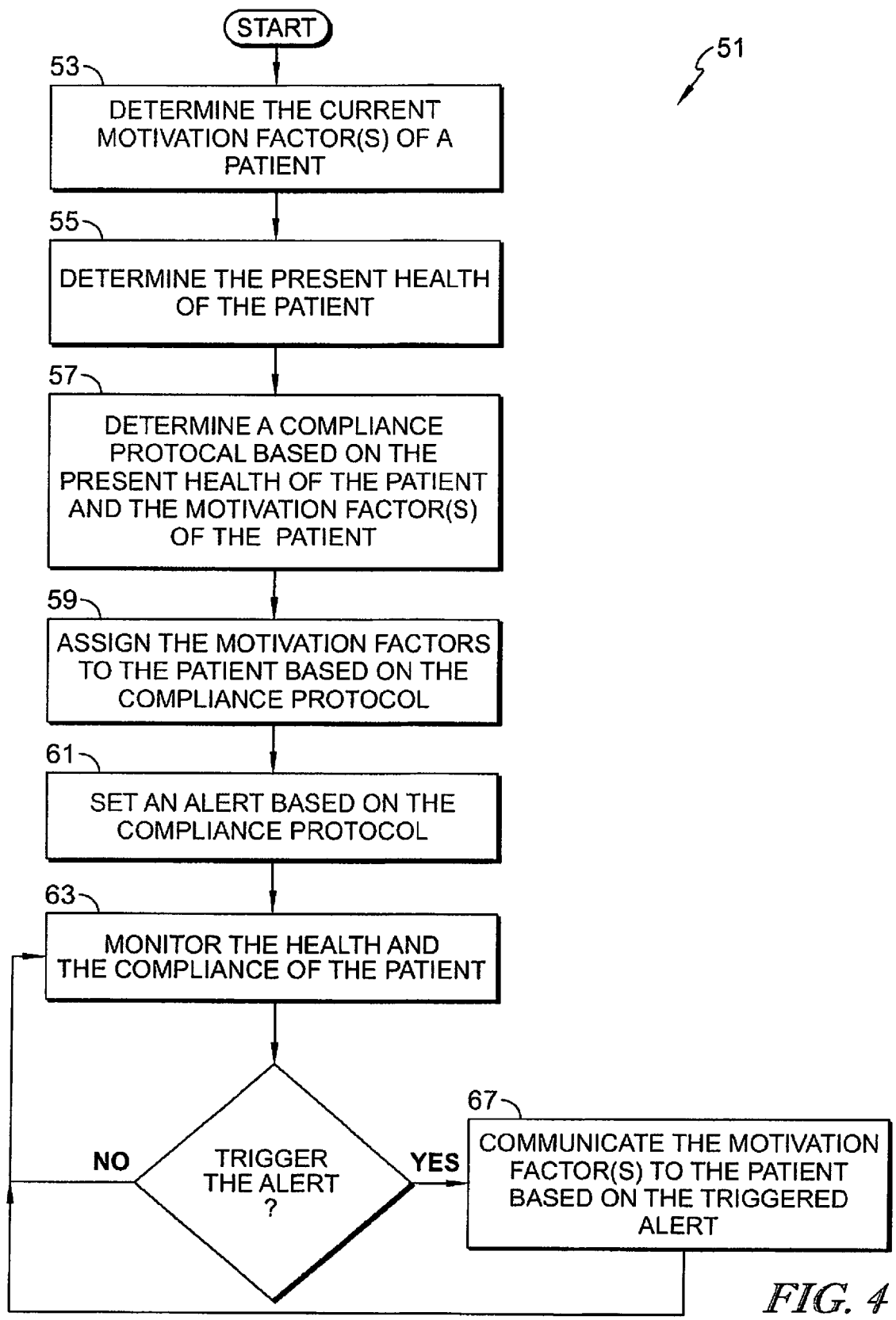
FIG. 4 is a process flow chart for a controller to determine a compliance protocol, monitor the health of the patient, and communicate a motivation factor(s) to the patient if the compliance protocol is violated.

The patient care hub 34 is configured to communicate data received by the sensors of the sensor system 26 to the patient interface 45 and ascertain from the sensed data whether the patient 10 is progressing towards a programmed health/care goal and, further, provide feedback to the patient 10 to prompt him/her/them to partake in an activity or update the patient 10 on his/her/their progress. The programmed health goal is created using a compliance determination algorithm 51 as shown in FIG. 4. At step 53, the patient 10 answers a survey and/or provides information so that the patient's current motivation factors may be identified. Such motivation factors may include an upcoming important date (i.e.: a grandchild's birthday), a personal goal of the patient 10, and/or other similar positive objectives. The present health of the patient 10 is determined using the vital signs of the patient 10 and/or other metrics to measure the patient's health, at step 55. At step 57, a compliance protocol is determined based on the present health of the patient 10 and the patient's motivation factors. The motivation factors are assigned to the patient 10 based on the compliance protocol such that different motivation factors are communicated to the patient 10 in response how the patient's health is trending, at step 59. To explain, if the patient's health is negatively trending, the patient care hub 34 is configured to communicate a message to the patient 10 via the patient interface 45 including information such as a medical adherence tracker, motivating stories, and/or special dates. If the patient's health is positively trending, then the patient care hub 34 is configured to communicate reassuring feedback such as "Great Job!" or "Keep up the good work!" At step 61, at least one alert is set based on the compliance protocol so that the patient 10 will receive feedback in response to particular events in the patient's care plan. The patient care hub 34 is configured to continuously monitor the health and the compliance of the patient 10 to the compliance protocol, at step 63. At step 67, if while monitoring the patient 10 the alert is triggered, then the motivating factor associated with the violated compliance protocol is communicated to the patient 10 via the patient interface 45, at step 67. After alerting the patient 10 and/or the caregiver 24, the patient care hub 34 returns to monitoring the health of the patient 10 and the compliance of the patient 10 such that if the compliance protocol is violated a second time, the patient care hub 34 is configured to transmit a second message to the patient 10 and/or caregiver 24.

Additionally, the algorithm 51 shown in FIG. 4 may also be used to communicate feedback to the patient 10 concerning a violation of the care plan itself. The process in doing so is similar to that discussed above concerning feedback provided to the patient 10 concerning the patient's health, but the care plan is also evaluated when determining the compliance plan. This allows for the patient care hub 34 to communicate feedback to the patient 10 concerning a violation of the compliance protocol relating to the patient's care plan. For example, if the patient's care plan instructs the patient 10 to walk around his/her/their room every 5 hours, and the patient 10 has not exited the bed in 6 hours, then the patient care hub 34 is configured to communicate feedback to the patient 10 and/or the caregiver 24 including a reminder to the patient 10 to exit the bed in order to comply with his/her/their care plan. Further, medication adherence charts may also be included in the feedback to the patient interface 45 and further include data explaining how medication adherence impacts the patient's quality of life. By allowing the patient 10 to become involved in his/her/their own care, the patient 10 may become more compliant to his/her/their care plan.

In addition to medication adherence charts, the patient interface 45 is configured to further display a progress bar 186 as shown in FIG. 6. The progress bar 186 is configured to show the progress of the patient 10 through his/her/their care plan. The progress bar 186 may further show health markers 188 positioned on the progress bar 186 such that the patient 10 may identify the exact day during his/her/their treatment that he/she/they reached a health marker 188. The health markers 188 may include identifying when the patient 10 began feeling better, when the patient 10 reached enhanced mobility, etc. Further, a percentage of completion 190 may also be shown so that the patient 10 is aware of how far they have progressed. Informative labels/graphics 192 may also be used to convey the appropriate direction in which the progress bar 186 moves when the patient 10 is progressing well through his/her/their care plan. In additional contemplated embodiments of the patient interface 45, the progress bar 186 is configured to show the daily improvements/highlights of the patient 10. These daily updates may be combined with providing positive feedback and/or motivating factors to the patient 10 as previously discussed.

In additional embodiments of the patient care system 20, the patient care hub 34 is embodied as a tablet device 45 as shown in FIG. 7. Often when patient care is initiated the caregiver 24 will furnish the patient 10 and/or the patient's family a tablet device 45 or other digital device 45 that is configured to be the communication vehicle between the caregiver 24 and the patient 10. The tablet device 45 is configured to wirelessly communicate with the caregiver controller 43. The tablet device 45 is further configured to communicate with and/or collect data from the sensors of the sensor system 26 of the patient care system 20 as well as other physically and/or digitally connected devices (i.e.: spot monitors integrated with the siderail 15, scales electronically coupled to the patient care system 20). The tablet 45 is further configured to act as a key and activate the patient care system 20 and/or inform the patient care system 20 of the patient's identity. Once the patient's identity is confirmed, the patient care system 20 is configured to use the confirmed patient identity in all other digital communications transmitted from the patient care system 20 (i.e.: streaming the patient's vital signals or an emergency alert to the patient's identity. This allows for communication of the sensed data to the correct EMR record, the correct caregiver 24, or other data destination.

Figure 8:
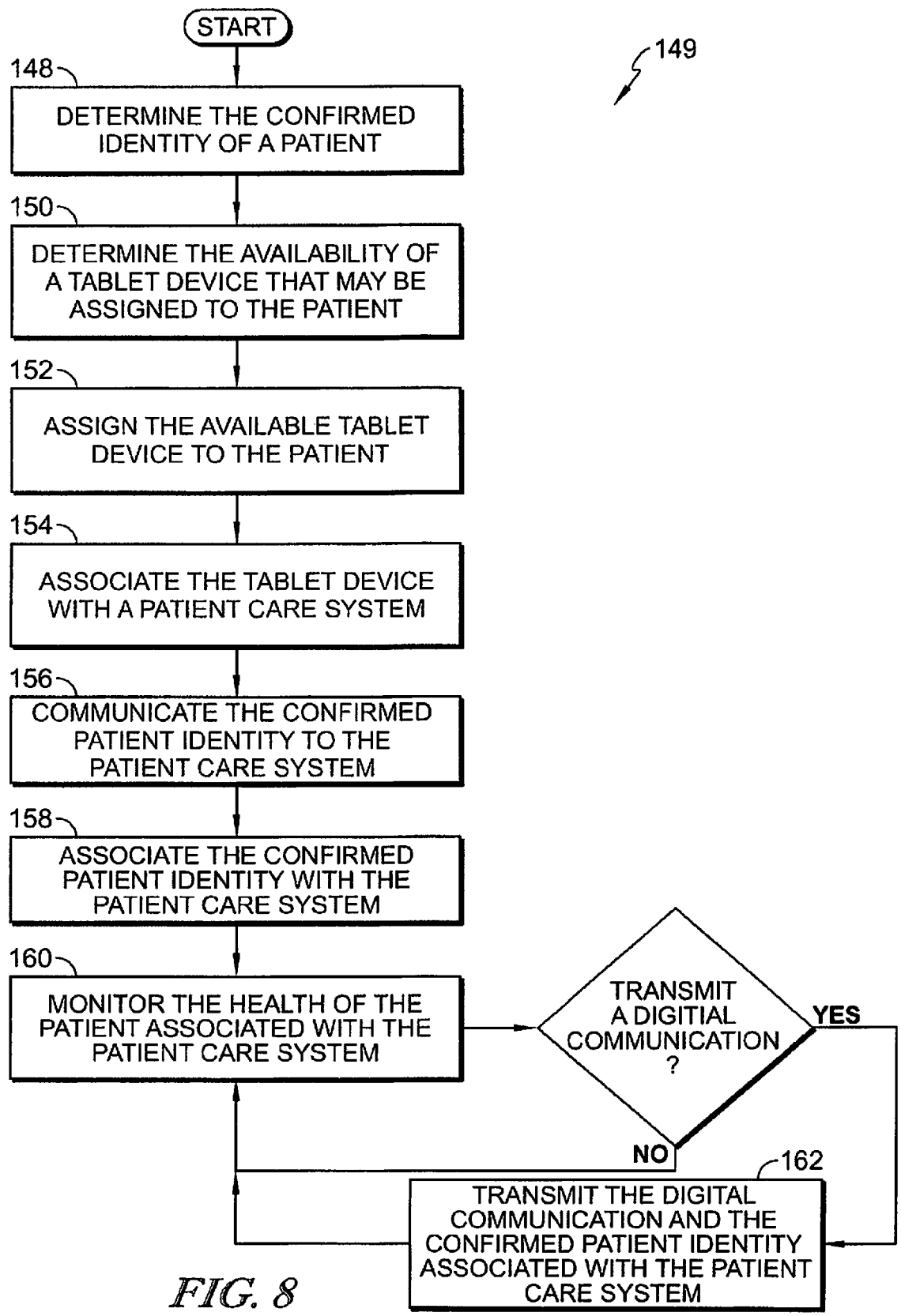
FIG. 8 is a process flow chart for a controller to assign a confirmed identity of a patient to a patient interface, associate the patient interface with the patient care system, and transmit a digital communication(s) from the patient interface with the confirmed identity of the patient also communicated.

As described in FIG. 8, to transform the tablet 45 into the key to activate the patient care system 20, a key activation algorithm 149 is programmed into the controller 40 of the of the patient care hub 34. The identity of the patient 10 is confirmed, at step 148. At step 150, the availability of the tablet device 45 to be assigned to the patient 10 is confirmed. The caregiver 24 assigns the available tablet device 45 to the confirmed patient 10, at step 152. At step 154, the tablet device 45 is associated with the patient care system 20. The confirmed identify of the patient 10 is communicated to the patient care system 20, at step 156. The tablet device 45 may be physically coupled to the patient support apparatus 12 and/or siderail 15 via a siderail dock 128, as suggested in FIG. 7, or digitally via electrical pairing as further discussed below. At step 158, the patient's identity is associated with the patient care system 20 and is configured to be used as metadata associating the designated patient identify with any data associated with the assigned patient care system 20. The patient 10 is continuously monitored by the patient care system 20 to monitor the health of the patient 10 associated with the patient care system 20 using the sensors of the sensor system 26, at step 160. At step 162, if while monitoring the patient 10 the patient care system 20 is instructed to transmit a digital communication, then the patient care system 20 transmits the digital communication with the confirmed patient identity associated with the patient care system 20. Once the digital communication is transmitted, the patient care system 20 returns to step 160 and continues monitoring the health of the patient 10 associated with the patient care system 20. Additionally, the tablet device 45 is configured to be prepopulated with the patient identify upon confirmation and association of the identity of the patient 10. This allows for simplified deployment of the patient care system 20. Further, correctly identifying and communicating the patient's identify with all digital communications allows for more accurate documentation in EMR and/or medication management.

Figure 9:
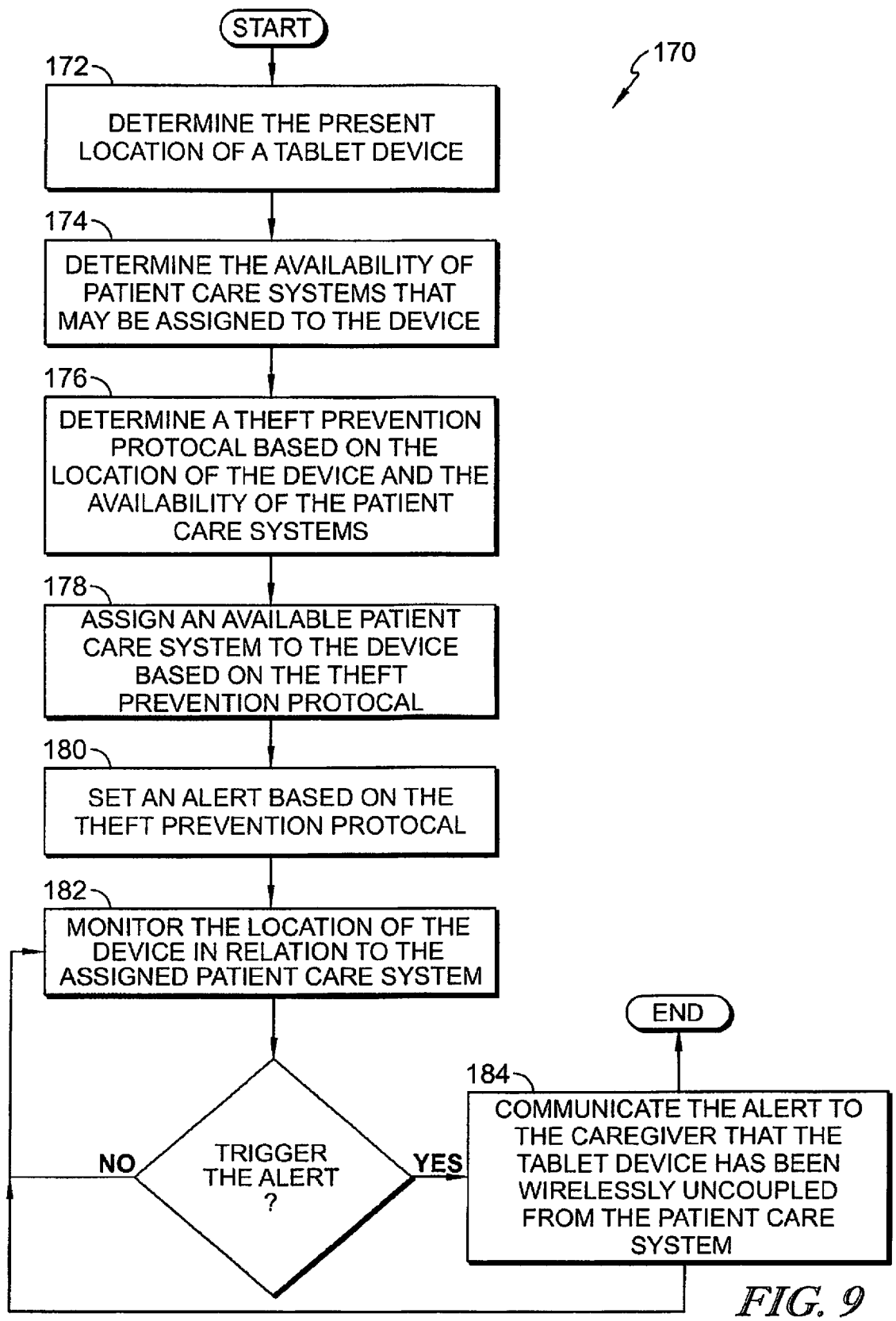
FIG. 9 is a process flow chart for a controller to determine a theft prevention protocol, monitor the location of the patient interface, and communicate an alert to the caregiver if the theft prevention protocol is violated.

The tablet device 45 is configured to permit patient communication with the caregiver 24, as discussed above, and is susceptible to theft due to the high expense of the tablet device 45. As such, it is desirable to protect against theft of the device 45. Illustratively, the tablet 45 is configured to be in digital communication with the patient care system 20 regarding the presence and/or location of the tablet device 45. An algorithm 170 configured to determine a theft-prevention protocol is programmed into the patient care hub 34 such that the patient care hub 34 is configured to locate the device 45, track the device 45, and alert a caregiver 24 that the device 45 is no longer in digital communication with the patient care system 20, as described in FIG. 9. To digitally couple the tablet 45 to the patient care system 20, the patient care system 20 determines the present location of the device 45, at step 172. At step 174, the device 45 identifies available patient care systems 20 that may be assigned to the device 45. A theft prevention protocol is determined by the patient care system 20 based on the location of the device 45 and the patient care systems 20 available, at step 176. At step 178, the device 45 is assigned to one of the available patient care systems 20 based on the theft prevention protocol such that the device 45 must remain in close proximity to the assigned patient care system 20 to avoid triggering an alert. The alerts are set based on the theft prevention protocol, in step 180. At step 182, the location of the tablet device 45 is continuously monitored by the patient care system 20. If the tablet 45 is wirelessly uncoupled from the patient care system 20, the patient care system 20 communicates the alarm to the caregiver 24 informing the caregiver 24 that the device 45 has been digitally uncoupled from the patient care system 20, at step 184. After alerting the caregiver 24, the patient care system 20 returns to monitoring the location of the device 45 and provide additional alerts if necessary.

In additional embodiments, the tablet device 45 is physically coupled to the patient care system 20 such that the tablet 45 cannot be removed from the patient care system 20 without a removal means such as an authorized code, a mechanical lock, and/or a special tool. As shown in FIG. 7, illustratively, the tablet device 45 is configured to couple to the siderail 15 of the patient care system 20 via the siderail dock 128. Illustratively, the siderail dock 128 includes an anchor 130 coupled to the rear surface of the tablet 45 and an anchor receiver 132 coupled to the siderail 15. The anchor 130 is configured to engage the anchor receiver 132 such that the tablet 45 cannot be removed from the patient support apparatus 12 without the use of a proper removal means. Other attachment means known in the art may also be used. The tablet 45 remains configured to be in electronic communication with both the sensors of the sensor system 26 and the caregiver controller 43.

Figure 10:
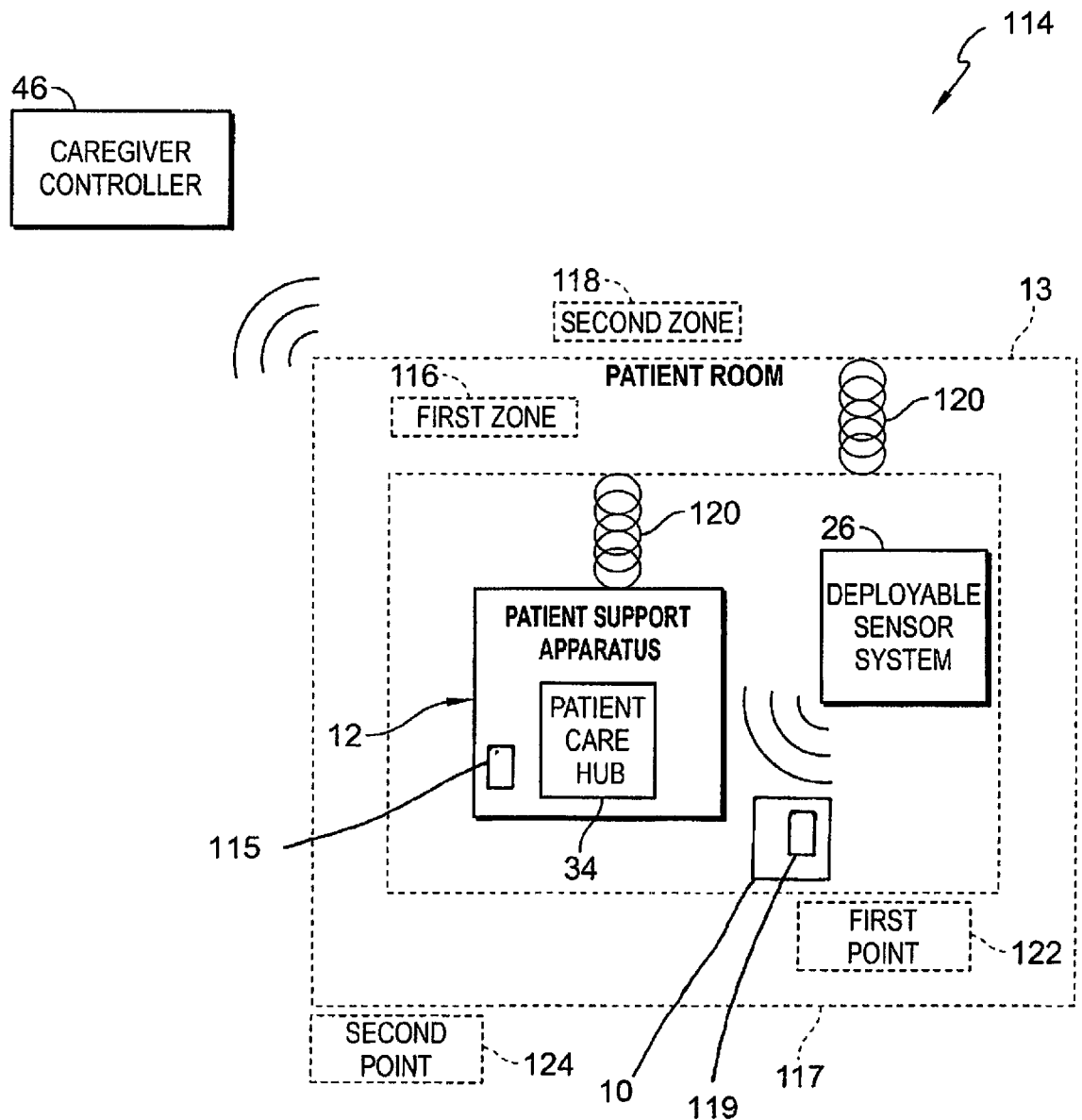
FIG. 10 is a schematic view of an illustrative embodiment of the deployable sensor system configured to determine the proximity of the patient to the patient care hub within two identified zones to locate the patient relative to the two identified zones and communicate the location of the patient to the caregiver controller.

The patient care system 20 is further configured to allow the caregiver 24 to monitor the movement/location of the patient 10 in relation to the patient support apparatus 12 using a patient monitoring system 114 as shown in FIG. 10. The proximity of the patient 10 to the patient support apparatus 12 informs the caregiver 24 of patient movement and the length of time the patient 10 has been in a particular zone 116, 118 of the room 13 and/or out of his/her/their bed 12. In order to determine the proximity of the patient 10 to the bed 12, the patient monitoring system 114 includes a transmitter 115, a perimeter wiring 117, and a receiver 119. The transmitter 115 is removeably coupled to the patient support apparatus 12 and configured to emit a signal to the perimeter wiring 117 and determine how far the electric field extends from the wiring 117. The perimeter wiring 117 is positioned to create a first zone 116 and a second zone 118 and configured to transform the signal into electromagnetic waves. As shown in FIG. 10, the first zone 116 is located between a first point 122 and the perimeter wiring 117. Illustratively, the first point 122 is a bathroom connected and adjacent to the patient's room 13. The second zone 118 is located outside of the first zone 116 and extends away from the patient's room 13 such that a second point 124 is positioned within the first zone 116. Illustratively, the second point 124 is an exit from the patient's room 13. The perimeter wiring 117 is configured to receive the signal from the transmitter 115 removeably coupled to the patient support apparatus 12 to create the boundaries of the first zone 116 and the second zone 118. The receiver 119 is removeably coupled to the patient 10 and configured to receive the signal from the perimeter wiring 117 when in close proximity to the wiring 117 to identify the location of the patient 10 within the zones 116, 118. Further, the patient monitoring system 114 may be configured to alert a caregiver 24 when the patient 10 initiates movement and/or when the patient 10 has been in a particular zone for an extended period of time. This alerts the caregiver 24 to a potential fall risk and allows for the remote monitoring of patients 10 as they move about their bedroom 13 and bathroom 122.

To allow for patient movement between the patient's bed 12, the first point 122, and the second point 124, the patient monitoring system 114 further includes at least one twisted wire 120 positioned within the patient's room 13. Illustratively, the patient monitoring system 114 includes at least two twisted wires 120 positioned in the patient's room 13 and configured to electrically couple the transmitter 115 and the perimeter wiring 117 thereby canceling the signal from the transmitter 115. One of the twisted wires 120 is located between the patient support apparatus 12 and the perimeter wiring 117 identifying the start of the first zone 116, illustratively. A second twisted wire 120 is located within the first zone 116 extending the perimeter wiring 117 identifying the start of the second zone 118. The twisted wire 120 is configured to cancel the signal from the perimeter wiring 117 such that the signal is blocked from reaching the receiver 119, thereby allowing the patient 10 to move between the zones 116, 118 without alerting the caregiver 24 of his/her/their movement or location. Illustratively, the transmitter 115 and the receiver 119 are embodied as a RFID sensor 26. Additionally, a bedside camera 26 may be used to detect motion of the patient 10 and/or the RFID sensor 26 may be used to activate the bedside camera 26.

Figure 11:
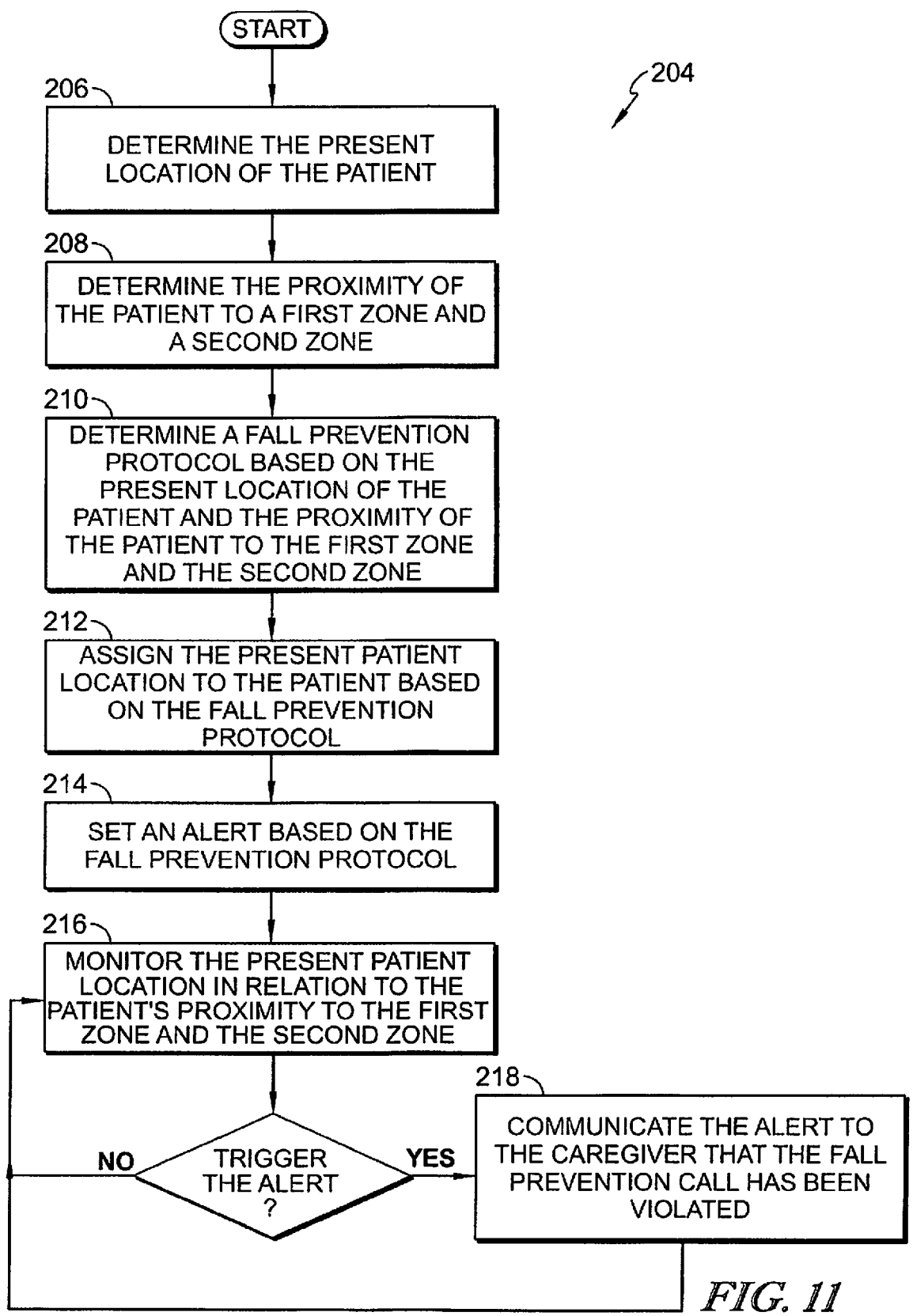
FIG. 11 is a process flow chart for a controller to determine a fall prevention protocol, monitor the location of the patient relative to the two identified zones, and communicate an alert to the caregiver if the fall prevention protocol is violated.

To determine if the patient 10 has moved and/or the location of the patient 10, a fall prevention algorithm 204 is programmed into the controller 40 of the patient care hub 34, as shown in FIG. 11. The present location of the patient 10 is determined, at step 206. At step 208, the patient monitoring system 114 further determines the proximity of the patient 10 to the first zone 116 and/or the second zone 118. The patient care hub 34 determines a fall prevention protocol based on the determined present location of the patient 10 and the proximity of the patient 10 to the first zone 116 and/or the second zone 118, at step 210. At step 212, the present location of the patient 10 is assigned to the patient 10 based on the fall prevention protocol. An alert(s) is set based on the fall prevention protocol, at step 214. At step 216, the present patient location is continuously monitored by the patient monitoring system 114 to locate the patient 10 in relation the first zone 116 and/or the second zone 118. If the patient 10 violates the fall prevention protocol, then an alert is sent to caregiver 24 via the caregiver controller 43 that the fall prevention protocol has been violated, at step 218. The alert may communicate additional information such as the present patient location and/or the amount of time the patient has been away from the patient support apparatus 12. Illustratively, the patient monitoring system 114 is removeably coupled to the patient support apparatus 12.

Figure 12:
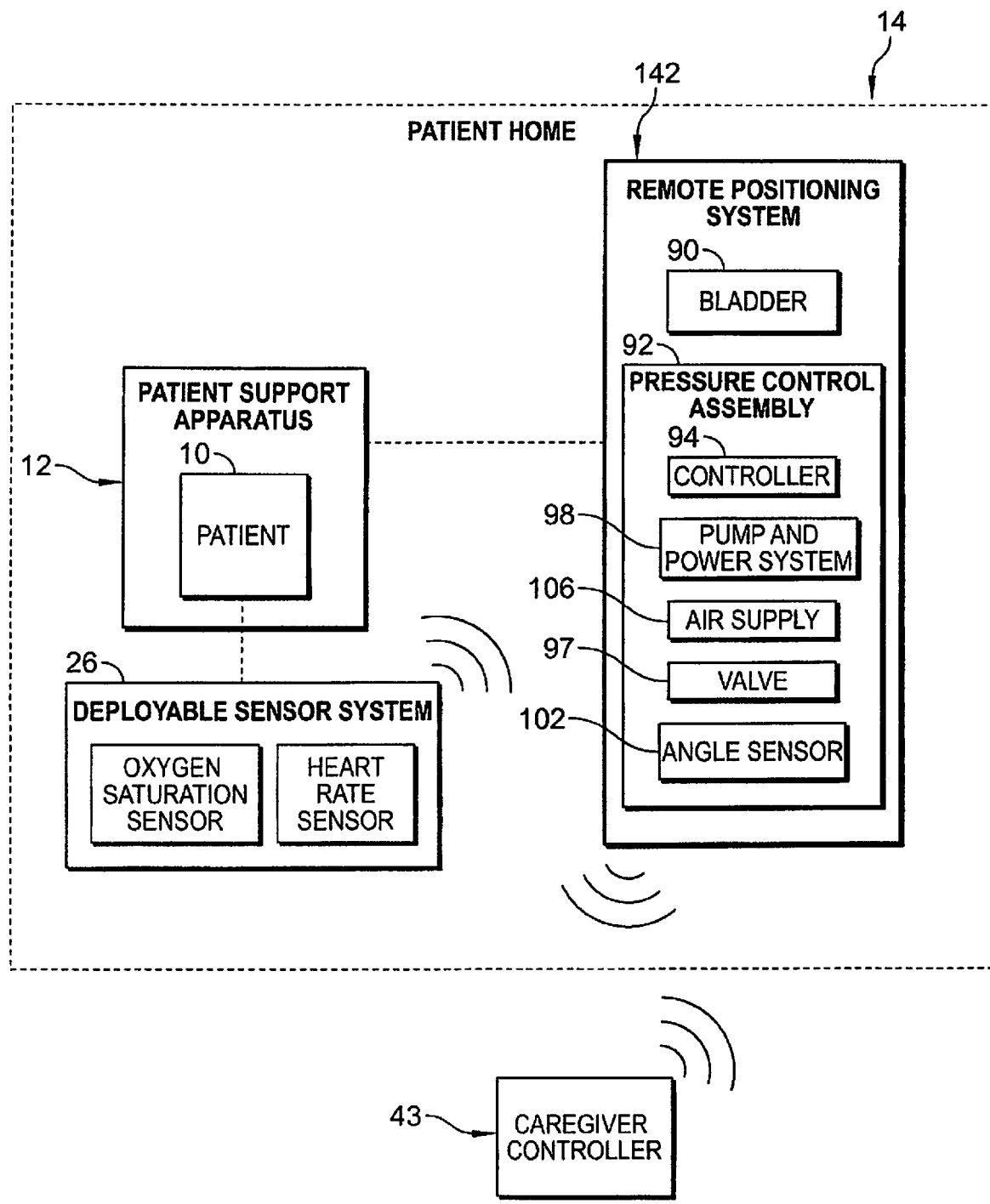
FIG. 12 is a diagrammatic view showing a positioning system removeably coupled to the patient support apparatus and configured to wirelessly communicate with the caregiver controller suggesting that the caregiver may control the remote positioning system when the caregiver is located outside of the patient's home.

The patient care system 20 is further configured to include a remote positioning system 142 that controls inflation and deflation of at least one inflatable bladder 90 positioned under a section 73, 78 of the mattress 22 as shown in FIGS. 12 and 13. The remote positioning system 142 includes at least one inflatable bladder 90 and a pressure control assembly 92. The inflatable bladder 90 is configured to be positioned between the mattress 22 and the base 18 of the patient support apparatus 12 such that the mattress 22 is located on top of the bladder 90, as shown in FIG. 13. The pressure control assembly 92 is in electrical communication with the caregiver controller 43 and the bladder 90 and includes a bladder controller 94, a pump/power system 98, an angle sensor 102, a bladder control valve 97, and an air source 106.

The inflatable bladder 90 may be positioned under only the head section 78 of the mattress 22 and configured to raise and lower the head section 78 relative to the seat section 76 and/or the frame 16. In other embodiments, the bladder 90 is positioned under only the foot section 73 of the patient support apparatus 12 and configured to raise and lower the foot section 73 relative to the seat section 76 and/or the frame 16. As illustratively shown in FIG. 12, the remote positioning system 142 may include two inflatable bladders 90. Illustratively, the first bladder 90 is positioned under the head section 78 and the second bladder positioned under the foot section 73. The pressure control assembly 92 is configured to be in electrical communication with the caregiver controller 43 and the patient interface 45 and inflate or deflate the bladder 90 to the desired angle 104 and firmness by controlling the air system 126 to adjust the amount of air directed into the bladder 90. Additionally, the caregiver controller 43 is configured to be used selectively and individually by the caregiver 24 to control the pressure control assembly 144 to adjust the angle 104 of each zone 75, 77 of the mattress 22 independent of each other. Further, the display screen 46 on the GUI of the caregiver controller 43 is configured to illustrate the two sections 73, 78 of the mattress 22, and each section 73, 75 has an input option such that the caregiver 24 may input the desired angle 104 of each section 73, 75 independent of the other. In some embodiments, the mattress 22 may include more than two moveable sections.

The bladder controller 94 is in communication with the caregiver controller 43 and the air pump/power system 98 and configured to control the air source 106 to vary the pressure in the air bladder 90. To do so, the bladder controller 94 is configured to respond to an input by the caregiver 24 into the caregiver controller 43 concerning the amount of air provided by the air supply 106 as shown in FIGS. 12 and 14. To explain, if the caregiver 24 increases the angle of the bladder 104, then the bladder controller 94 receives this input and instructs the air pump 98 to increase the amount of air supplied by the air source 106 and directs an air flow into the bladder 90 via a conduit 99 coupling the air pump 98, the air source 106, a bladder control valve 97, and the bladder 90. Once the angle sensor 102 coupled to the bladder 90 reaches the desired angle 104, the bladder controller 94 communicates the angle 104 to the air pump 98 to stop pulling air from the air source 106. Conversely, if the caregiver 24 decreases the angle of the bladder 104, then the bladder controller 94 will receive this input and instruct the bladder control valve 97 to open and release air contained in the bladder 90 until the desired angle 104 is detected by the angle sensor 102. Once the desired angle 104 is reached, the angle sensor 102 communicates the angle 104 to the bladder controller 94, and the bladder controller 94 communicates to the air pump 98 to stop pulling air from the air source 106. Due to the electrical communication between the caregiver controller 43 and the pump controller 94, the bladders 90 located in the foot section 73 and the head section 75 are configured to be positioned independent of each other.

As shown in FIG. 12, the sensor(s) 26 are further configured to be removeably coupled to the patient 10 and in electronic communication with the patient care hub 34. The remote caregiver 24 will receive an alert from the patient care system 20 concerning a low heart rate and/or low oxygen saturation via the caregiver controller 43 if the heart rate and/or oxygen saturation falls below a programmed threshold. As previously discussed, the sensors of the sensor system 26 are in electronic communication with the caregiver controller 43 and are configured to alert the caregiver 24 of a violation of the predefined parameters programmed into the bladder controller 94. This allows for the caregiver 24 to communicate an instruction to the bladder controller 94 regarding inflating or deflating the bladder 90 while the caregiver 24 is located remotely. In additional embodiments, the patient 10 may communicate to the caregiver 24 via the patient interface 45 a desire for the head and/or foot section 78, 73 to be raised or lowered. Upon receiving the communication from the patient 10, the caregiver 24 may remotely inflate or deflate the bladder(s) 90 to the patient's desired angle 104 as described in FIG. 15.

Figure 15:
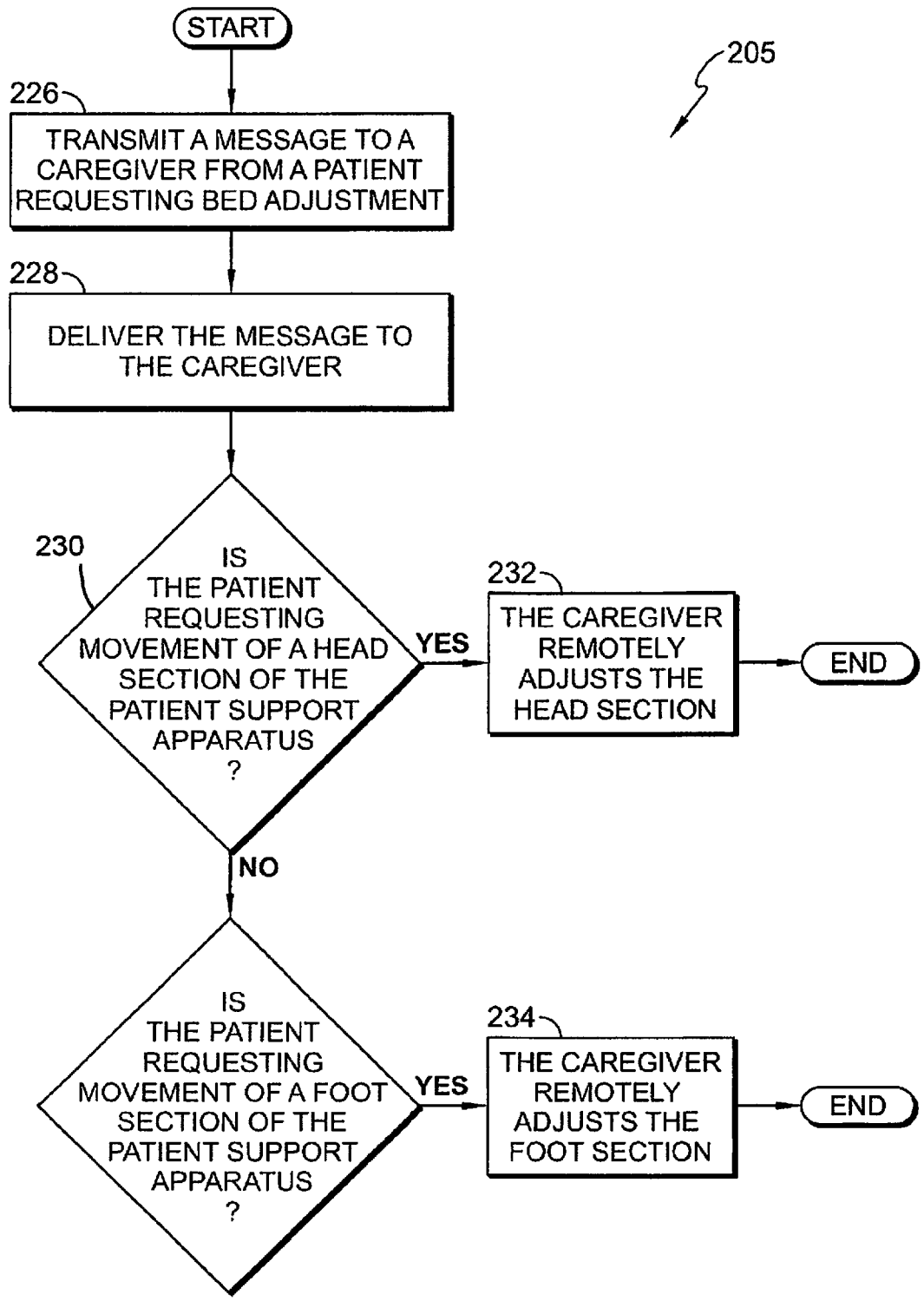
FIG. 15 is a process flow chart for a caregiver to remotely adjust the head section and/or foot section of the mattress in response to a request from the patient.

To determine if the patient 10 desires movement of the patient support apparatus 12, a movement request algorithm 205 is programmed into the system 20 as shown in FIG. 15. At step 226, the patient 10 transmits a message to the caregiver 24 requesting movement of the bed. The message is delivered to the caregiver 24, at step 228. At step 230, the caregiver 24 determines if the patient 10 is requesting movement of the head section 78. At step 232, if the patient 10 is requesting movement of the head section 78, then the caregiver 24 obliges and moves the head section 78 via the bladder controller 94. If the patient 10 is requesting movement of the foot section 73, then the caregiver 24 obliges and moves the foot section 73, at step 234. The process of remotely inflating or deflating the bladder(s) 90 is substantially similar to the process described above concerning the remote adjustment of the bladder(s) 90 by the caregiver 24 to a desired angle as well as an adjustment by the caregiver 24 in response to the violation of a predefined parameter of the bladder controller 94.

An illustrative embodiment of the remote positioning system 142 is configured to measure the oxygen saturation level of the patient 10, automatically adjust the patient 10 in response to a respiratory decline, and communicate an alert to the caregiver 24 if the patient's respiratory function continues to decline following the automatic patient adjustment. The bladder controller 94 is configured to automatically adjust the patient 10 when the patient 10 is unable to alert the caregiver 24 of respiratory issues such as when the patient 10 is asleep, unconscious, or otherwise physically unable to communicate with the caregiver 24 and a predefined parameter of the bladder controller 94 is violated. To determine if the parameter has been violated, the bladder controller 94 is in electronic communication with the sensors of the sensor system 26, illustratively coupled to the patient 10 and embodied as a pulse oximeter 26, and configured to receive data concerning the oxygen saturation level of the patient 10. The predefined parameters of the bladder controller 94 are configured to identify when the patient's oxygen saturation level is below 90% saturation and act upon this sensed data to automatically attempt to increase the oxygen saturation level of the patient 10.

Figure 16:
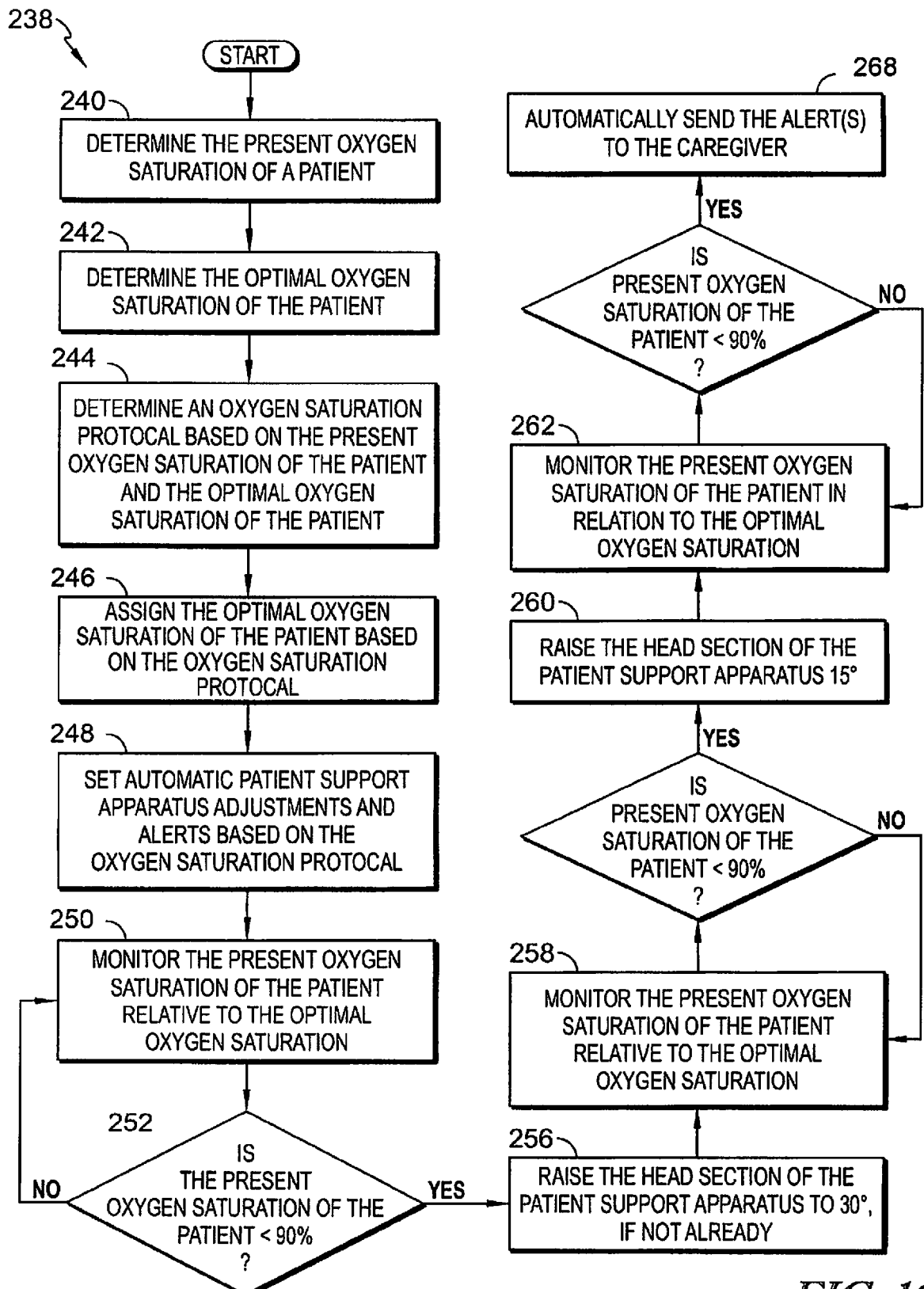
FIG. 16 is a process flow chart for a controller to determine an oxygen saturation protocol, monitor the oxygen saturation of the patient, automatically adjust the angle of the head section of the mattress in response to a violation of the oxygen saturation protocol, and communicate an alert to the caregiver if the oxygen saturation prevention protocol is violated at least three times.

To explain, and as illustrated in FIG. 16, in illustrative embodiments, an oxygen saturation level stabilization algorithm 238 is programmed into the bladder controller 94. The present oxygen saturation level of the patient 10 is measured by the sensors of the sensor system 26 and communicated to the bladder controller 94, at step 240. At step 242, the bladder controller 94 determines the optimal oxygen saturation level of the patient 10. An oxygen saturation level protocol is determined based on the present oxygen saturation level of the patient 10 and the optimal oxygen saturation level of the patient 10, at step 244. At step 246, the optimal oxygen saturation level of the patient 10 is assigned to the patient 10 based on the oxygen saturation level protocol. The threshold(s) are set concerning the oxygen saturation level at which the patient support apparatus 12 automatically adjusts and/or alerts the caregiver 24 based on the oxygen saturation protocol, at step 248. At step 250, the patient 10 is continuously monitored by the bladder controller 94 in electronic communication with the sensors of the sensor system 26. The bladder controller 94 determines whether the current oxygen saturation level of the patient 10 is less than 90%, at step 252. At step 256, if the current oxygen saturation level is below 90%, then the head section 78 of the patient support apparatus 12 is automatically raised to 30°. The bladder controller 94 returns to continuously monitoring the patient 10, at step 258. At step 260, if the current oxygen saturation level is below 90%, then the head section 78 of the patient support apparatus 12 is automatically raised to 15°. The bladder controller 94 returns to continuously monitoring the patient 10 at step 264. The bladder controller 94 determines whether the current oxygen saturation level of the patient 10 is less than 90% after the first automatic adjustment, at step 262. At step 268, if the current oxygen saturation level is still below 90% after the second automatic adjustment, then an alert is automatically sent to the caregiver 24. In configuring the remote positioning system 142 to automatically adjust the patient 10, the caregiver 24 may expedite the release the patient 10 from the health care facility and continue his/her/ their care plan in the patient's home 14.

Figure 17:
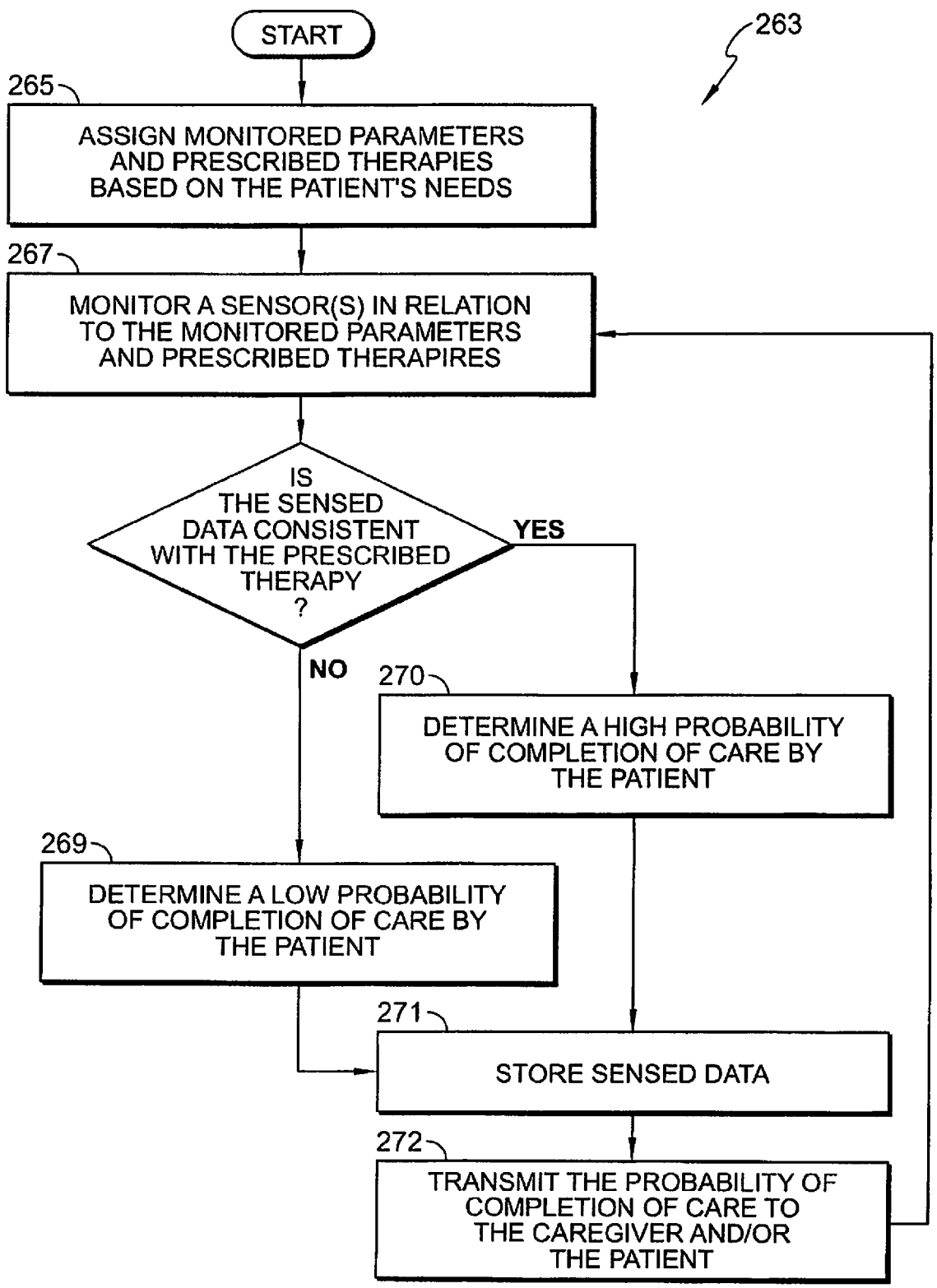
FIG. 17 is a process flow chart for a controller to compare the assigned monitored parameters with the prescribed therapies and patient needs to determine the probability of completion of care by the patient.

As previously discussed, the patient care hub 34 is configured to act as a centralized monitoring, communications, and reporting system and is embodied as a centralized hub enabled for electronic communication (i.e.: a smart speaker). Illustratively, the patient care hub 34 is further configured to assess the probability of completion of care by a patient 10 by comparing the interaction of the patient 10 and the patient assistance device 30 related to patient's the care plan as described in FIG. 17. To do so, the patient assistance device 30 is removeably coupled to the agnostic sensor 26. The sensor 26 is in electronic communication with the patient care hub 34 and is configured to communicate sensed data measured by the sensor 26. The patient care hub 34 receives the sensed data from the sensor 26 and compares is to the thresholds programmed into the patient care hub 34 regarding the care plan of the patient 10. The patient care hub 34 determines whether the sensed data is consistent with the programmed therapy to determine the probability of completion of care by the patient 10.

To determine the probability of completion of care, a probability of completion algorithm 263 is programmed into the controller 40 of the patient care hub 34. The monitored parameters and prescribed therapies of the patient 10 are assigned to the controller 40 of the patient care hub 34, at step 265. At step 267, the patient 10 is continuously monitored by the sensors of the sensor system 26 in relation to the monitored parameters and prescribed therapies. The controller 94 determines whether there is a low probability of completion of care by the patient 10 based on comparing the consistency of the sensed data with the prescribed therapies, at step 269. The controller 94 determines whether there is a high probability of completion of care by the patient 10 based on comparing the consistency of the sensed data with the prescribed therapies, at step 270. At step 271, the sensed data is stored in the patient care hub 34. The probability of completion of care by the patient 10 is transmitted to the caregiver 24 via the caregiver controller 43 and/or the patient 10 via the patient interface 45, at step 272.

To explain, in an illustrative example, if an accelerometer 26 is removeably coupled to an incentive spirometer 30 and the patient 10 has been instructed to complete breathing exercises, then the caregiver 24 will program the patient care hub 34 to compare sensed data from the accelerometer 26 to a desired, programmed threshold to determine whether the sensed data is consistent with the proscribed therapy. If the sensed data shows a short period of rapid movement of the incentive spirometer, then it is unlikely to have resulted from its use for a breathing exercise due to the short period of use. The patient care hub 34 uses this sensed data to determine the patient's probability of completion of care and transmit this information to the caregiver 24.

In an additional example, a first accelerometer 26 is coupled to a walker 30 and a second accelerometer 26 is coupled to the patient 10 so that the patient's movement may be compared to the motion of the walker 30. The patient care hub is configured to determine that if the patient 10 has not moved but the walker 30 has, then the patient 10 is not using the walker 30. Additionally, more than one sensor 26 may be in communication simultaneously with the patient care hub 34. Further, each sensor 26 may be coupled to distinct patient assistance devices 30 and/or the patient 10 as the patient care hub 34 is configured to communicate with each sensor 26 and synthesize the sensed data to determine various probability of completion concerning each individual therapy. A total probability of completion concerning the entire care plan may also be determined by the patient care hub 34. Other patient assistance devices 30 include sequential compression devices (SCD) 30, walker assistance devices 30, and other health monitoring devices known in the art. Further, other sensors of the sensor system 26 include power use sensors, motion sensors, touch sensors, and sensors detecting that packaging is opened or used.

The patient care hub 34 is further configured to remotely unlock an entrance to the patient's home 14 in response to a command from the patient 10 entered into the patient interface 45. The patient care hub 34 in electronic communication with a door entry mechanism 136 coupled to the entrance of the patient's home 14, the caregiver controller 43, and the patient interface 45 and configured to communicate an alert to the patient interface 45 upon the caregiver's arrival. The patient care hub 34 is further configured to communicate a command entered into the patient interface 45 by the patient 10 to the door entry mechanism 136 to unlock the entrance and allow the caregiver 24 entry into the patient's home 14. The patient care hub 34 is configured to receive the command from the patient interface 45 and compare it to thresholds programmed into the patient care hub 34 regarding an unlock protocol assigned to the patient's home 14. The patient care hub 34 is further configured to determine the presence of the caregiver 24 and the location of the entrance into the patient's home 14 to notify the patient 10 when the caregiver 24 is present at an entrance to the patient's home 14. The patient care hub 34 is further configured to identify the command of the patient interface 45 and determine if an unlock command has been entered into the patient interface 45. If an unlock command has been entered, then the patient care hub 34 is configured to remotely unlock the door entry mechanism 136, thereby avoiding the need for the patient 10 to exit the patient support apparatus 12 and physically unlock the door entry mechanism 136.

Figure 18:
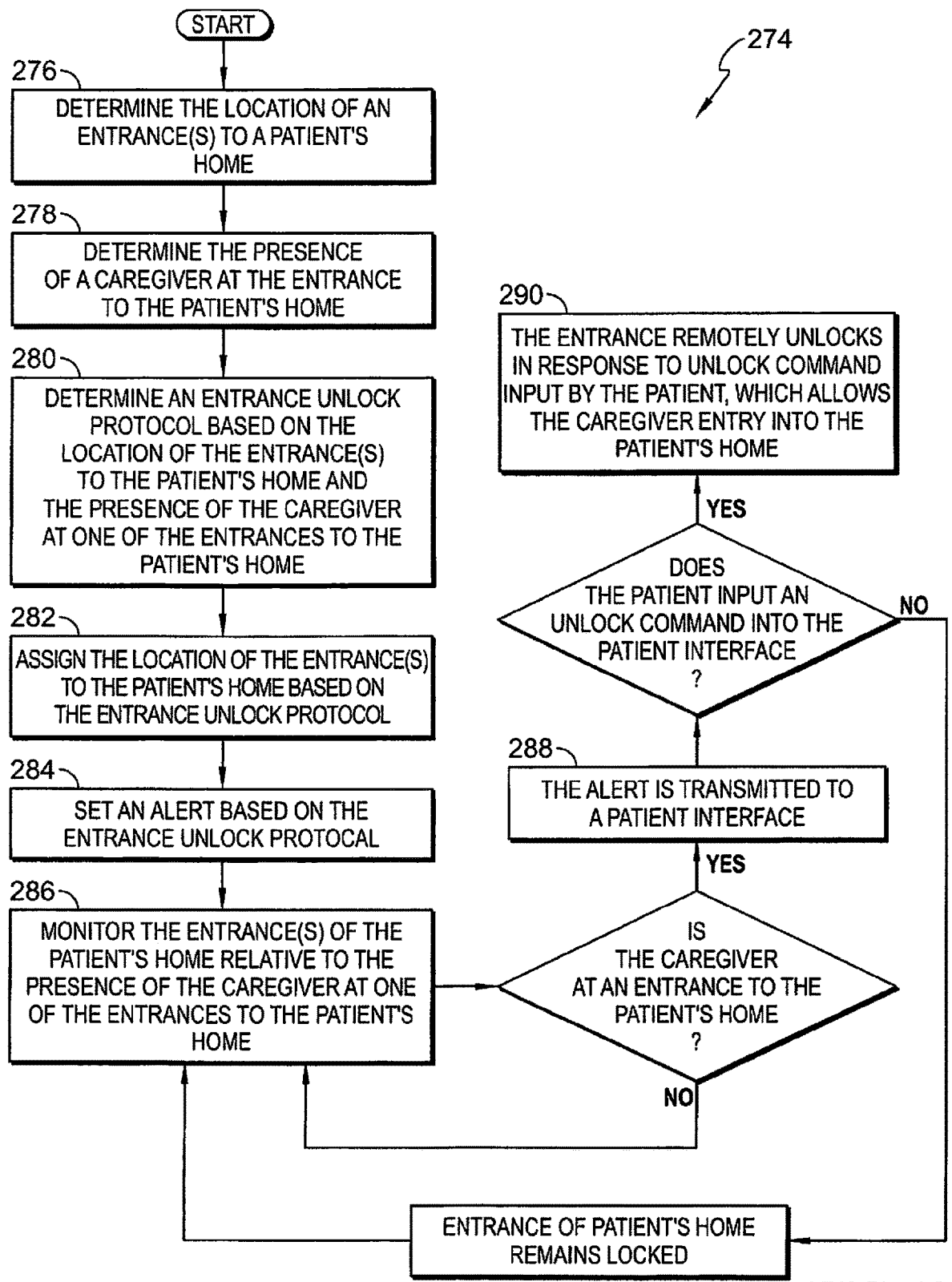
FIG. 18 is a process flow chart for a controller to determine an entrance unlock protocol, monitor the location of the entrance(s) to the patient's home and the presence of the caregiver at the entrance to the patient's home, communicate an alert to the patient if the entrance unlock protocol has been violated, and communicate an unlock command input by the patient to unlock a door entry mechanism.

To determine if the entrance should be unlocked, an entrance unlock algorithm 274 is programmed into the controller 40 of the patient care hub 34 as described in FIG. 18. The location of the entrance(s) to the patient's home 14 is determined, at step 276. At step 278, the presence of the caregiver 24 at one of the entrance(s) to the patient's home 14 is determined. The patient care hub 34 determines an entrance unlock protocol based on the location(s) of the entrance(s) to the patient's home 14 and the presence of a caregiver 24 at one of the entrance(s), at step 280. At step 282, the monitored entrance(s) are assigned based on the entrance unlock protocol. An alert is set based on the entrance unlock protocol at step 284. At step 286, the entrance is continuously monitored by a sensor(s) 26 to identify when the caregiver 24 is present. If the caregiver 24 is at the entrance to the patient's home 14, then an alert is sent to the patient 10 via the patient interface 45 allowing the patient 10 to remotely unlock the entrance, at step 288. At step 290, if the patient inputs an unlock command into the patient interface 45 in response to the alert, then the patient care hub 34 communicates with the door entry mechanism 136 to remotely unlock the entrance to the patient's home 14. If the patient 10 does not respond to the alert or inputs a lock command, then the entrance remains locked and the sensors of the sensor system 26 return to monitoring the entrance(s).

Although this disclosure refers to specific embodiments, it will be understood by those skilled in the art that various changes in form and detail may be made without departing from the subject matter set forth in the accompanying claims.

The invention claimed is:

1. A patient care system, comprising:
 a deployable sensor system including an at least one sensor configured to monitor a patient and wirelessly communicate a plurality of sensed data during a treatment program,
 a patient care hub including a patient hub controller, a processor, and a memory device including instructions that, when executed by the processor, cause the patient care hub to receive the plurality of sensed data from the at least one sensor, process the sensed data, discern patient activity, monitor the sensed data, and wirelessly communicate the sensed data and discerned activity of the patient,
 a patient interface including a speaker, a microphone, and a display, and configured to communicate wirelessly with the patient care hub, and
 a caregiver controller including a speaker, a microphone, a display, a processor, a memory device, and a communication device configured to communicate wirelessly with the patient care hub and the patient interface,
 wherein the patient care hub controller is distinct from the caregiver controller, and
 wherein the patient interface and caregiver controller are operable to display the progress of the patient relative to the treatment program on a respective progress bar displayed on the respective display of the patient interface and the caregiver controller,
 wherein the memory device of the patient care hub includes further instructions that, when executed by the processor, (i) prompt the patient to enter information on the patient interface and (ii) to use the sensed data and information entered by the patient to provide prompts to the patient to provide feedback to the patient during the progression of the treatment program, and
 wherein the memory device of the patient care hub includes further instructions that, when executed by the processor, remotely unlock an entrance to the patient's home in response to a command entered into the patient interface.

2. The patient care system of claim 1, further comprising an at-home positioning system configured to communicate wirelessly with the caregiver controller and operable to adjust the patient supported on a patient support apparatus.

3. The patient care system of claim 2, wherein the at-home positioning system comprises:
 at least one inflatable bladder positioned to provide support for a patient when the patient is positioned on at least a portion of the patient support apparatus, and
 a pressure-control assembly operably coupled to the at least one inflatable bladder and configured to regulate a pressure within the at least one inflatable bladder, wherein the pressure-control assembly includes a programmable controller configured to communicate wirelessly with the caregiver controller and operable to monitor a sensed pressure value of a fluid pressure within the at least one inflatable bladder and adjust the fluid pressure within the at least one inflatable bladder in response to a plurality of instructions from the caregiver controller.

4. The patient care system of claim 3, wherein the programmable controller is further configured to communicate wirelessly with the deployable sensor system, receive a plurality of sensed data from the sensor system, discern a patient health status, compare the patient health status to an at least one predefined parameter, and communicate an alert to the caregiver controller when the patient health status violates one of the at least one predefined parameters.

5. The patient care system of claim 4, wherein the at-home positioning system is configured to be remotely activated by the caregiver controller, the caregiver controller is configured to wirelessly communicate with a bladder controller configured to activate a pump, the pump is configured to direct a flow of air towards the at least one inflatable bladder.

6. The patient care system of claim 3, the at-home positioning system further including an angle sensor coupled to the at least one inflatable bladder and configured to wirelessly communicate an angle of the at least one inflatable bladder with the bladder controller, the bladder controller further configured to communicate with a pressure control valve configured to control a flow of air and change the angle of the at least one inflatable bladder.

7. The patient care system of claim 3, wherein the bladder controller is further configured to communicate wirelessly with the deployable sensor system, receive a plurality of signals from the sensor system, discern a patient health status, compare the patient health status to an at least one predefined parameter, and automatically adjust the at least one inflatable bladder in response to a violation of one of the at least one predefined parameters.

8. The patient care system of claim 7, wherein the at least one predefined parameter is oxygen saturation of the patient and the at least one sensor is configured to measure the oxygen saturation of the patient, the bladder controller is further configured to increase an angle of the at least one inflatable bladder positioned under a head section of the patient support apparatus to at least 30° relative to a seat section of the patient support apparatus in response to an oxygen saturation level less than 90%.

9. The patient care system of claim 7, wherein the at least one predefined parameter is oxygen saturation of the patient and the bladder controller is configured to increase an angle of at least one inflatable bladder positioned under a head section of the patient support apparatus to at least 45° relative to a seat section of the patient support apparatus if the oxygen saturation level is less than 90%.

10. The patient care system of claim 7, wherein the at least one predefined parameter is oxygen saturation of the patient and the bladder controller is configured to wirelessly communicate with the caregiver controller if the oxygen saturation level is less than 90% after increasing the angle of the at least one inflatable bladder positioned under a head section of the patient support apparatus to at least 45° relative to a seat section of the patient support apparatus.

11. The patient care system of claim 1, wherein the patient care hub is in electronic communication with a door entry mechanism coupled to the entrance of the patient's home.

12. The patient care system of claim 11, wherein the memory device of the patient care hub includes further instructions that, when executed by the processor, receives a command from the patient interface and compares the command to a threshold defined by an unlock protocol assigned to the patient's home.

13. A patient care system, comprising:
a deployable sensor system including an at least one sensor configured to monitor a patient and wirelessly communicate a plurality of sensed data during a treatment program,
a patient care hub including a patient hub controller, a processor, and a memory device including instructions that, when executed by the processor, cause the patient care hub to receive the plurality of sensed data from the at least one sensor, process the sensed data, discern patient activity, monitor the sensed data, and wirelessly communicate the sensed data and discerned activity of the patient,
a patient interface including a speaker, a microphone, and a display, and configured to communicate wirelessly with the patient care hub, and
a caregiver controller including a speaker, a microphone, a display, a processor, a memory device, and a communication device configured to communicate wirelessly with the patient care hub and the patient interface,
wherein the patient care hub controller is distinct from the caregiver controller, and
wherein the patient interface and caregiver controller are operable to display the progress of the patient relative to the treatment program on a respective progress bar displayed on the respective display of the patient interface and the caregiver controller,
wherein the memory device of the patient care hub includes further instructions that, when executed by the processor, (i) prompt the patient to enter information on the patient interface and (ii) to use the sensed data and information entered by the patient to provide prompts to the patient to provide feedback to the patient during the progression of the treatment program, and
wherein the memory device of the patient care hub includes further instructions that, when executed by the processor, monitor the location of a caregiver and notify the patient when the caregiver is present at the patient's home.

14. The patient care system of claim 13, wherein the memory device of the patient care hub includes further instructions that, when executed by the processor, remotely unlock an entrance to the patient's home in response to a command entered into the patient interface.

15. The patient care system of claim 14, wherein the patient care hub is in electronic communication with a door entry mechanism coupled to the entrance of the patient's home.

16. The patient care system of claim 15,
wherein the memory device of the patient care hub includes further instructions that, when executed by the processor, receives a command from the patient interface and compares the command to a threshold defined by an unlock protocol assigned to the patient's home.

17. The patient care system of claim 16, wherein the memory device of the patient care hub includes further instructions that, when executed by the processor, monitor the sensed data of the sensor system, compare the sensed data to a prescribed therapy, and make a determination of whether the data is consistent with the prescribed therapy.

18. The patient care system of claim 17, wherein the memory device of the patient care hub includes further instructions that, when executed by the processor, upon the determination of the consistency of the sensed data with the prescribed therapy, make a determination of the probability of the completion of care by the patient.

19. The patient care system of claim 18, wherein the memory device of the patient care hub includes further instructions that, when executed by the processor, transmits the probability of the completion of care by the patient to the caregiver.

20. A patient care system, comprising:
a deployable sensor system including an at least one sensor configured to monitor a patient and wirelessly communicate a plurality of sensed data during a treatment program,
a patient care hub positioned in proximity to the deployable sensor system, including a patient hub controller, a processor, and a memory device including instructions that, when executed by the processor, cause the patient care hub to receive the plurality of sensed data from the at least one sensor, process the sensed data, discern patient activity, monitor the sensed data, and wirelessly communicate the sensed data and discerned activity of the patient,
a patient interface including a speaker, a microphone, and a first display, and configured to communicate wirelessly with the patient care hub, and
a caregiver controller including a speaker, a microphone, a second display, a processor, a memory device, and a communication device configured to communicate wirelessly with the patient care hub and the patient interface,
wherein the caregiver controller is an electronic device,
wherein the patient care hub controller is distinct from the caregiver controller, and
wherein the patient interface and caregiver controller are operable to display the progress of the patient relative to the treatment program on a respective progress bar displayed on the first display of the patient interface and the second display of the caregiver controller, and
wherein the memory device of the patient care hub includes further instructions that, when executed by the processor, (i) prompt the patient to enter information on the patient interface so that a motivation factor may be identified and (ii) to use the sensed data and motivation factor to provide prompts to the patient to partake in an activity consistent with the treatment plan and the motivation factor and to provide feedback to the patient during the progression of the treatment program, wherein the memory device of the patient care hub includes further instructions that, when executed by the processor, monitor the sensed data of the sensor system, compare the sensed data to a prescribed therapy, and make a determination of whether the data is consistent with the prescribed therapy.

21. The patient care system of claim 20, wherein the memory device of the patient care hub includes further instructions that, when executed by the processor, upon the determination of the consistency of the sensed data with the prescribed therapy, make a determination of the probability of the completion of care by the patient.

22. The patient care system of claim 21, wherein the memory device of the patient care hub includes further instructions that, when executed by the processor, transmits the probability of the completion of care by the patient to the caregiver.

* * * * *